(12) United States Patent
Bar et al.

(10) Patent No.: US 10,595,899 B2
(45) Date of Patent: Mar. 24, 2020

(54) AUTOMATIC DILATOR

(71) Applicant: MAZOR ROBOTICS LTD., Caesarea (IL)

(72) Inventors: Yossi Bar, Tirat Carmel (IL); Eliyahu Zehavi, Haifa (IL); Yonatan Ushpizin, Kibbutz G'lil Yam (IL); Nadav Shoham, Hoshaya (IL)

(73) Assignee: MAZOR ROBOTICS LTD., Caesaria (IL)

( * ) Notice: Subject to any disclaimer, the term of this patent is extended or adjusted under 35 U.S.C. 154(b) by 876 days.

(21) Appl. No.: 15/023,409

(22) PCT Filed: Sep. 22, 2014

(86) PCT No.: PCT/IL2014/050845
§ 371 (c)(1),
(2) Date: Mar. 21, 2016

(87) PCT Pub. No.: WO2015/040623
PCT Pub. Date: Mar. 26, 2015

(65) Prior Publication Data
US 2016/0206347 A1 Jul. 21, 2016

Related U.S. Application Data

(60) Provisional application No. 61/880,953, filed on Sep. 22, 2013.

(51) Int. Cl.
*A61B 17/34* (2006.01)
*A61B 17/00* (2006.01)
(Continued)

(52) U.S. Cl.
CPC ...... *A61B 17/3421* (2013.01); *A61B 17/3476* (2013.01); *A61M 29/00* (2013.01);
(Continued)

(58) Field of Classification Search
CPC .. A61B 2017/00991; A61B 2017/3433; A61B 2017/3443; A61B 2017/3454;
(Continued)

(56) References Cited

U.S. PATENT DOCUMENTS

| 4,772,266 A | 9/1988 | Groshong et al. |
| 5,792,044 A | 8/1998 | Foley et al. |

(Continued)

OTHER PUBLICATIONS

PCT International Search Report and Written Opinion of the ISA, dated Jan. 15, 2015, in PCT/IL2014/050845.

*Primary Examiner* — Diane D Yabut
*Assistant Examiner* — Majid Jamialahmadi
(74) *Attorney, Agent, or Firm* — Sheridan Ross P.C.

(57) ABSTRACT

Automatic dilator devices for generating minimally invasive access apertures for surgical procedures or endoscopic surveillance. The automatic dilators comprise a number of spreader tubes nested one inside the other. The devices deploy automatically by means of coupled mechanical mechanisms which insert one spreader after the other distally into the patient's tissue. Each spreader moves distally into the tissue by means of a screwing action, by which rotation is converted into linear motion of the neighboring spreader, immediately external to it, by means of interaction between a helical thread form on a surface of a spreader being engaged by a section of thread, or by one or more protrusions on the opposing face of the next spreader external to the rotating spreader. Such a combination of helical thread and follower enables a rotatory mechanism to be used to deploy one nested spreader tube after the other, by continuous rotary motion.

17 Claims, 27 Drawing Sheets

(51) Int. Cl.
*A61B 34/30* (2016.01)
*A61M 29/00* (2006.01)

(52) U.S. Cl.
CPC ..... *A61B 34/30* (2016.02); *A61B 2017/00991* (2013.01); *A61B 2017/3433* (2013.01)

(58) Field of Classification Search
CPC . A61B 17/3421; A61B 17/3417; A61B 34/30; A61M 29/00; A61M 2025/0175
USPC ........................................................ 606/191
See application file for complete search history.

(56) References Cited

U.S. PATENT DOCUMENTS

| | | | |
|---|---|---|---|
| 7,811,303 B2 | 10/2010 | Fallin et al. | |
| 2005/0080443 A1* | 4/2005 | Fallin | A61B 17/3417 606/191 |
| 2007/0255305 A1 | 11/2007 | McMichael et al. | |
| 2008/0051821 A1 | 2/2008 | Gephart | |
| 2012/0232658 A1 | 9/2012 | Lopez | |
| 2013/0041398 A1 | 2/2013 | Goddard et al. | |
| 2013/0345718 A1* | 12/2013 | Crawford | A61B 17/025 606/130 |

\* cited by examiner

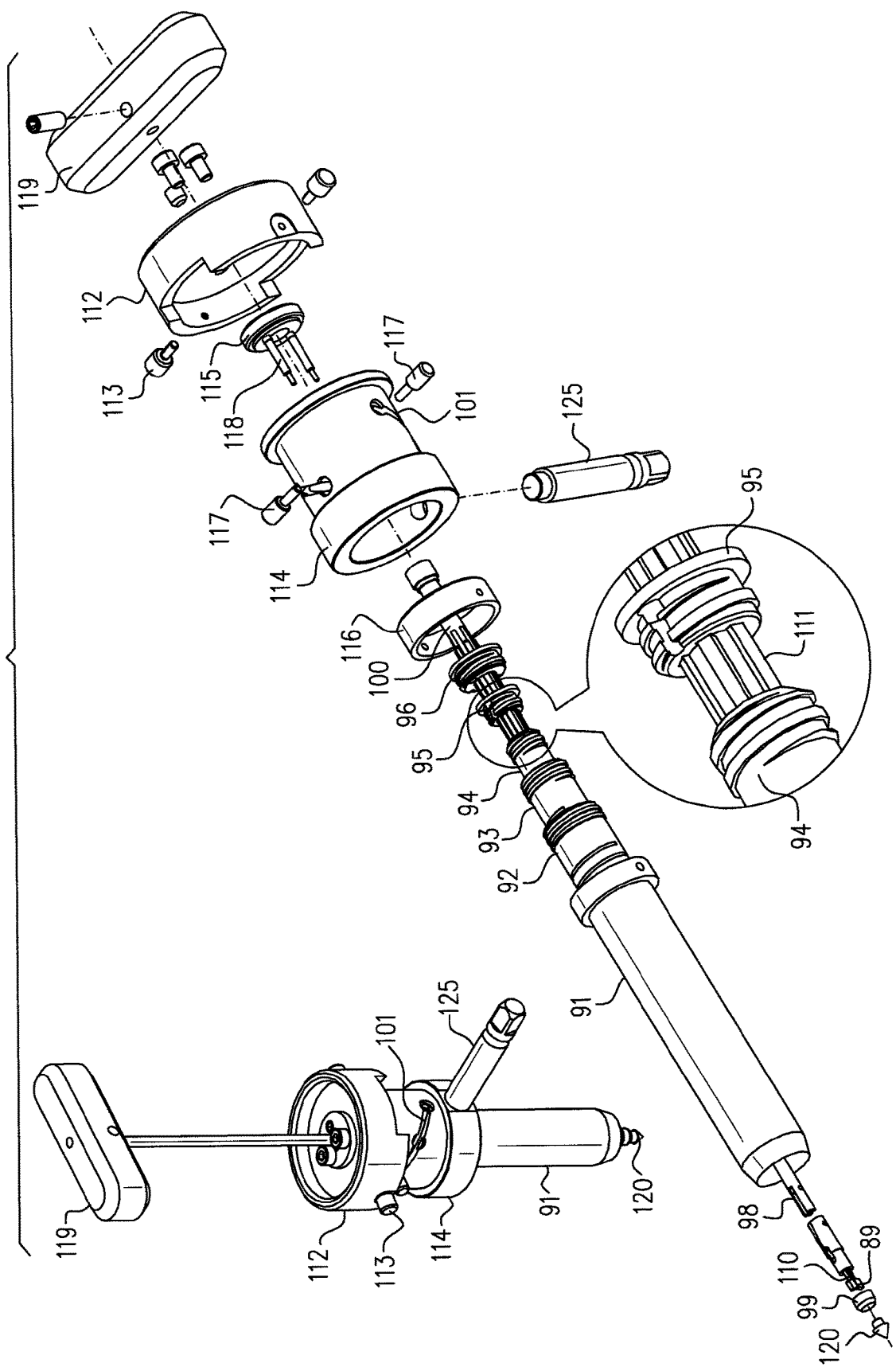

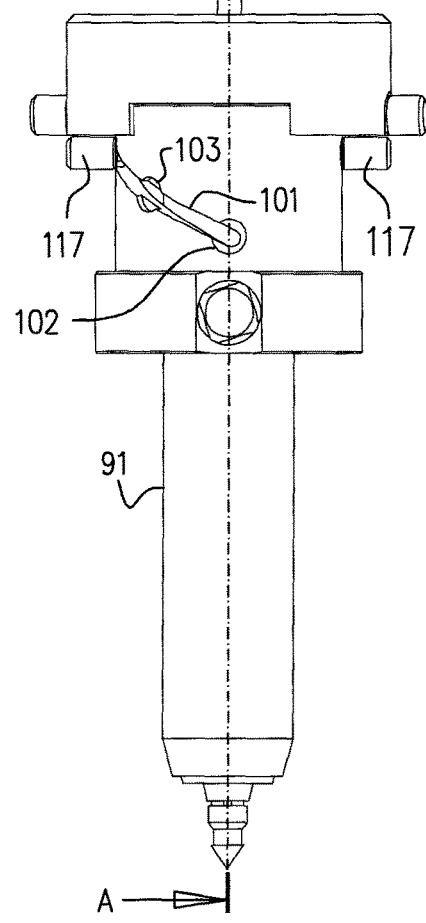
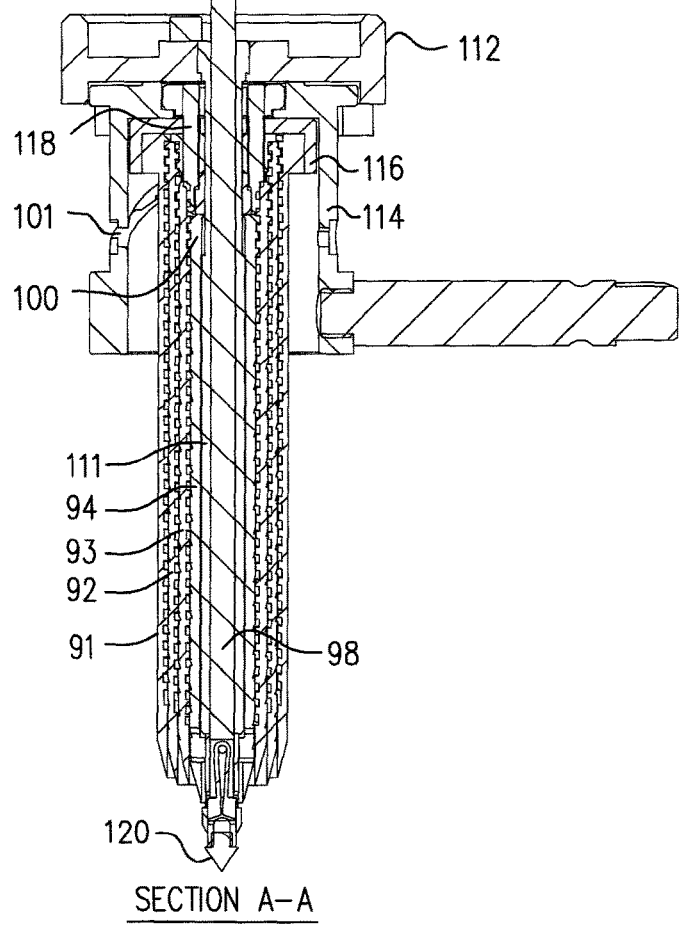

SECTION B-B

SECTION C-C

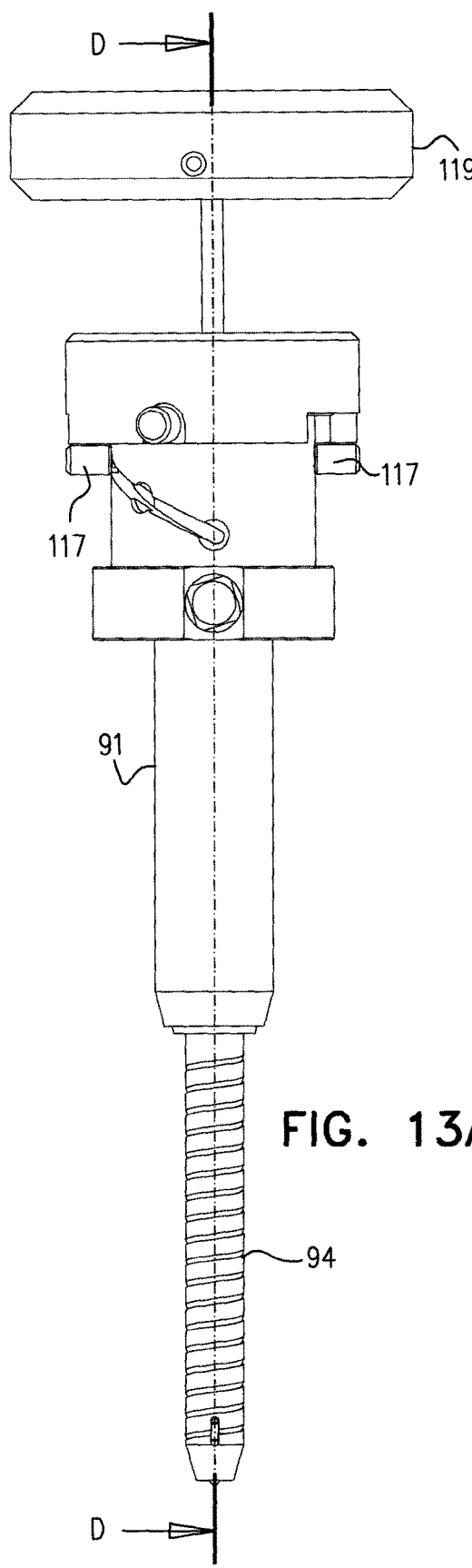
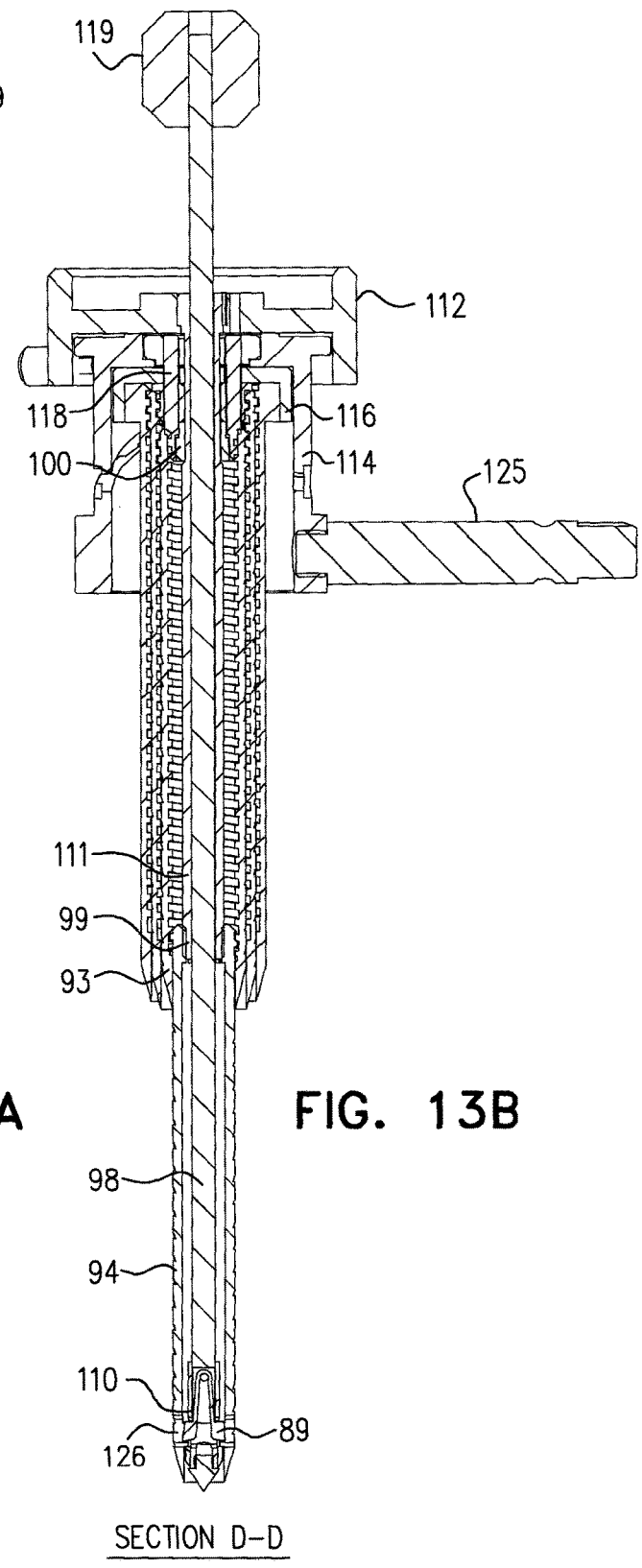
FIG. 13A
FIG. 13B
SECTION D-D

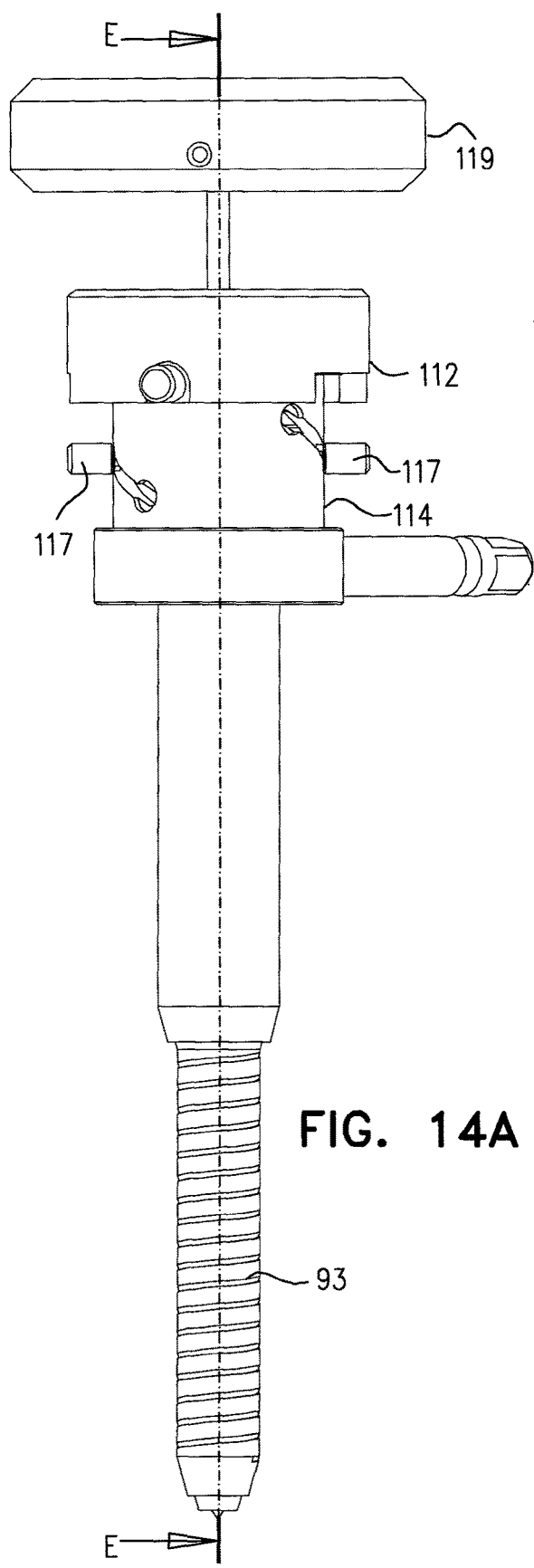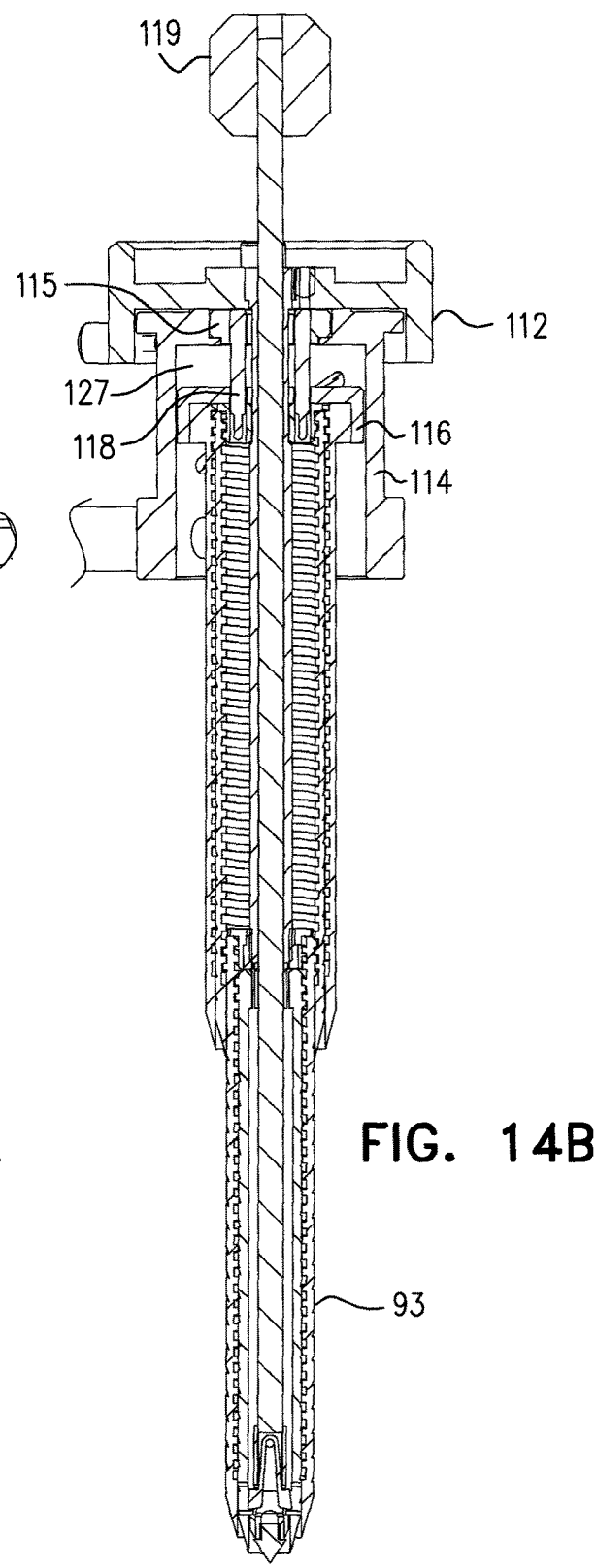
FIG. 14A
FIG. 14B
SECTION E-E

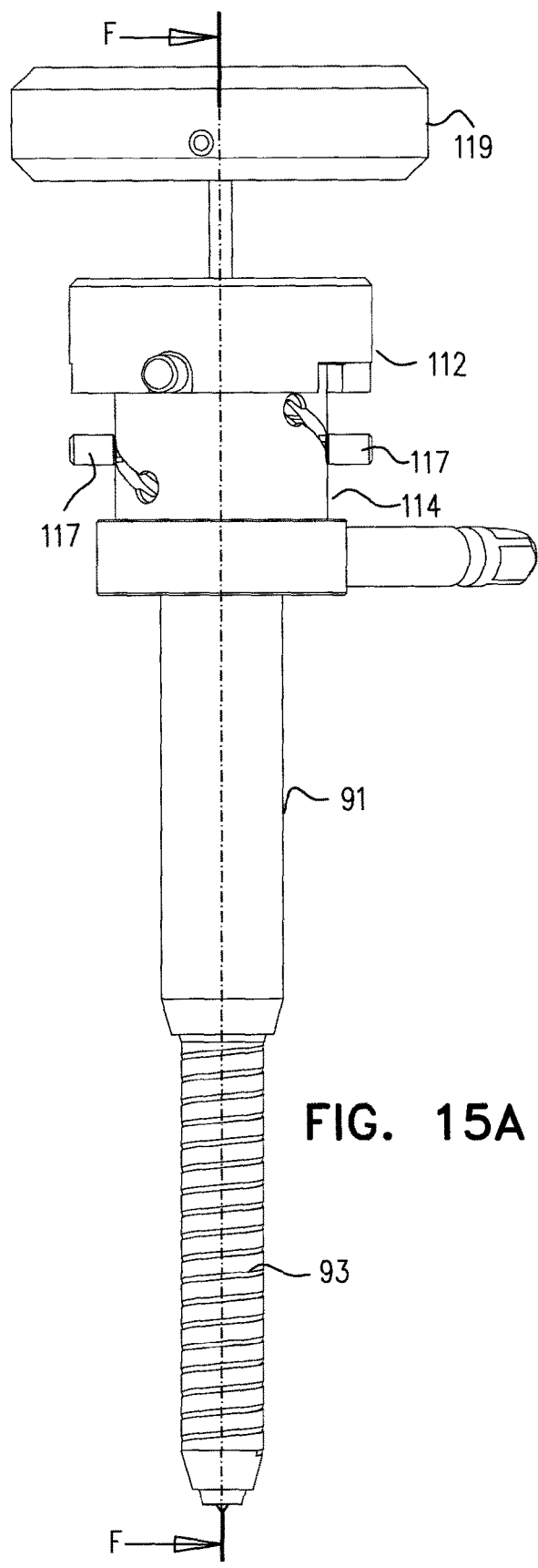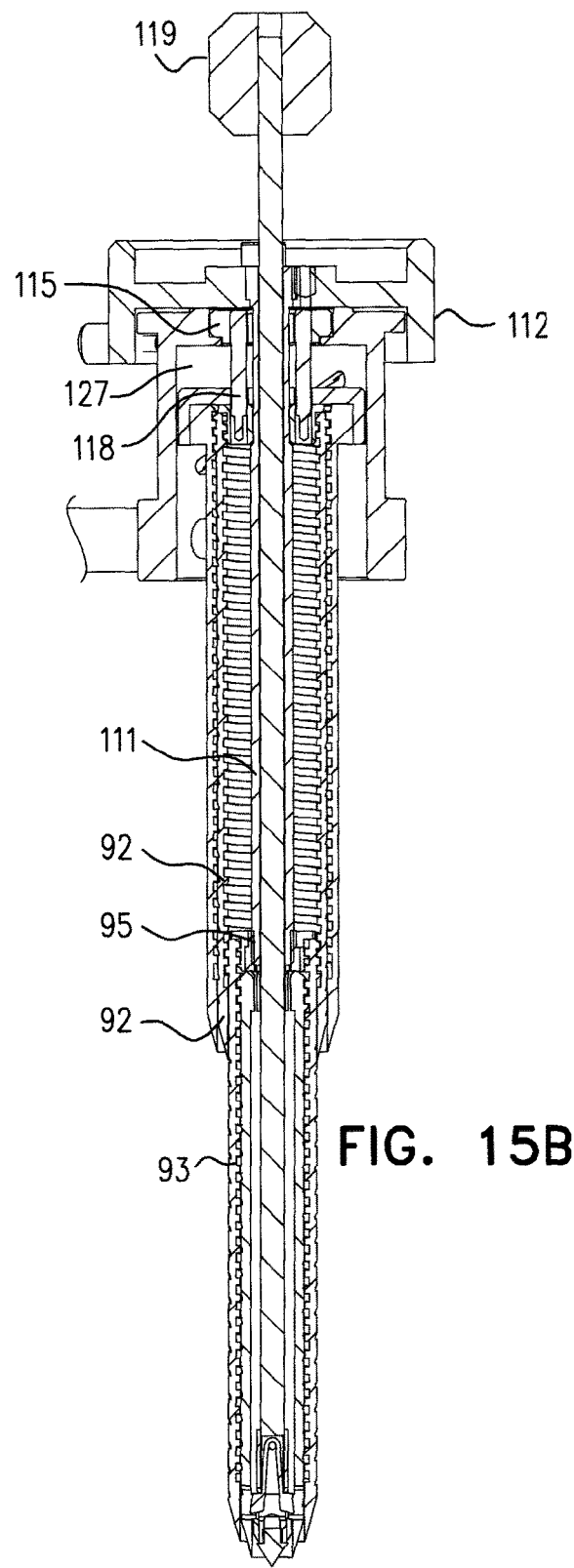

SECTION G-G

SECTION K-K

SECTION L-L

SECTION M-M

SECTION N-N

SECTION O-O

FIG. 23A
FIG. 23B
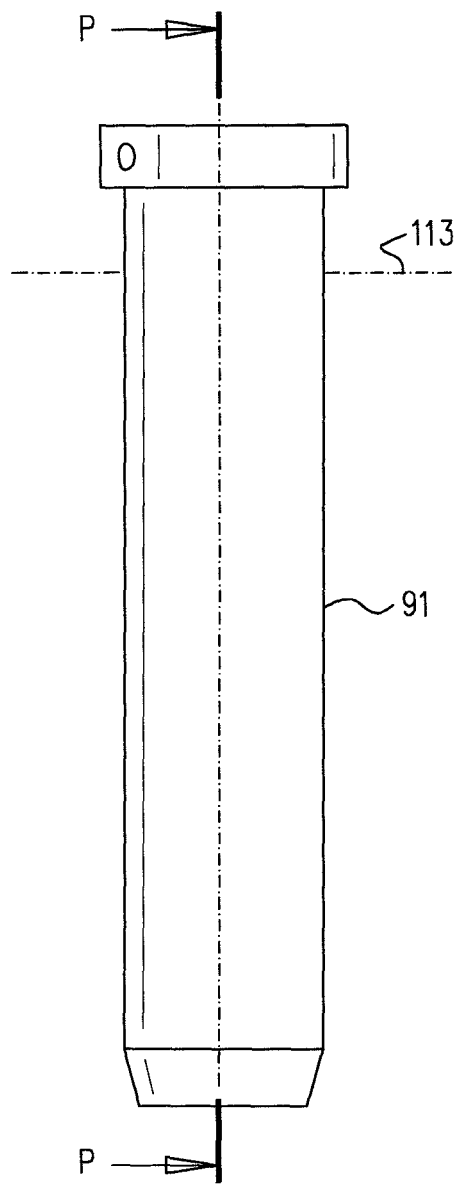
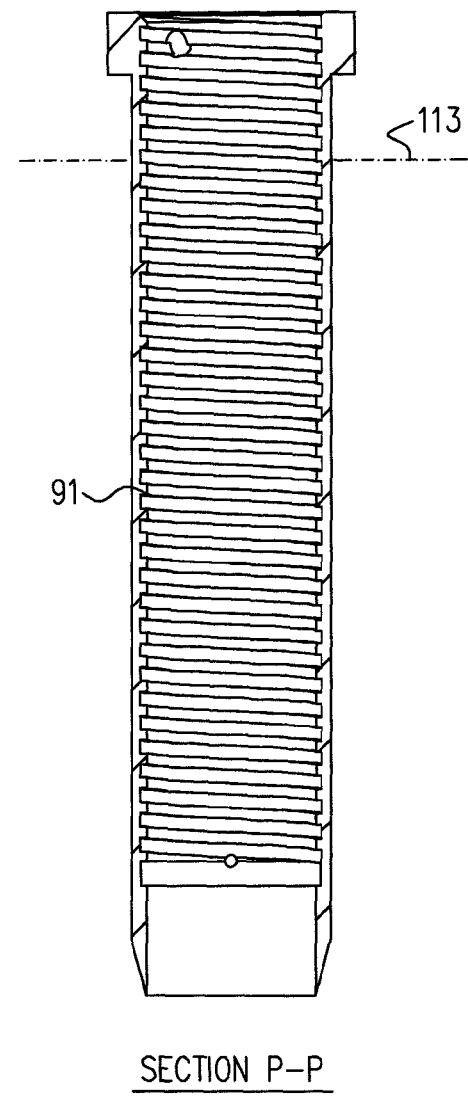
SECTION P-P

FIG. 25A
FIG. 25B
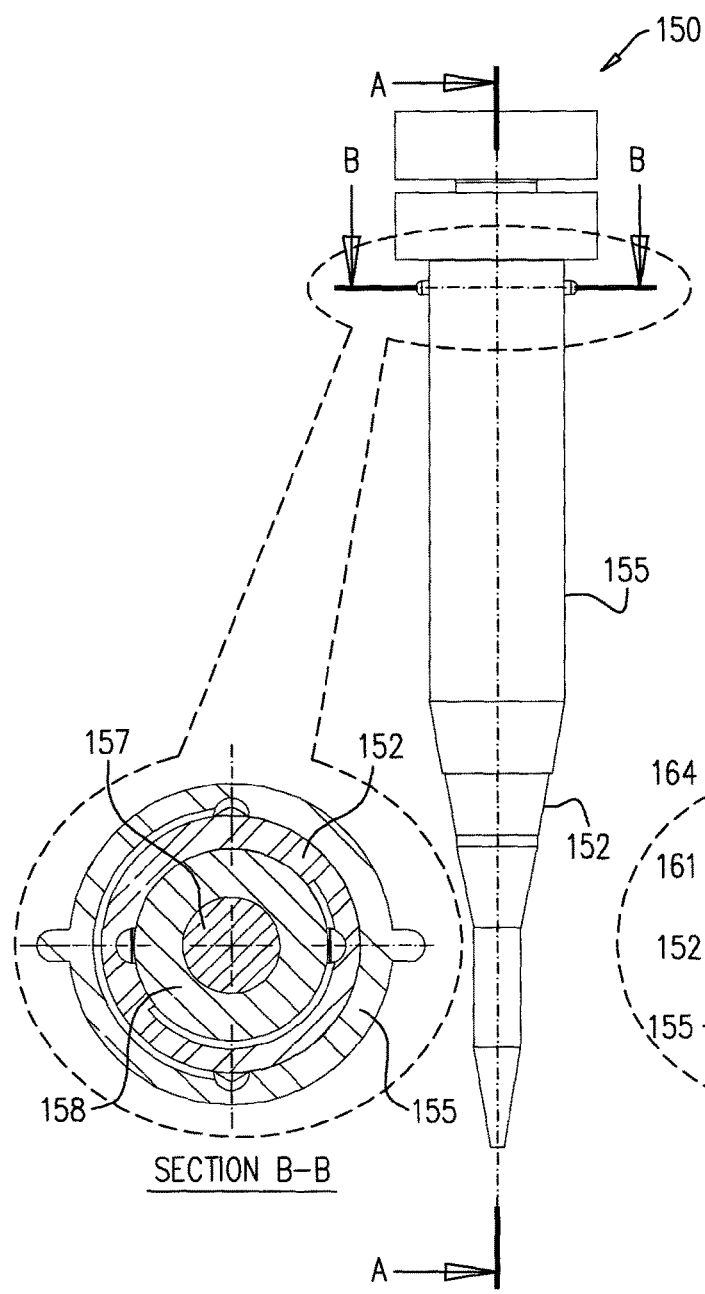
SECTION B-B
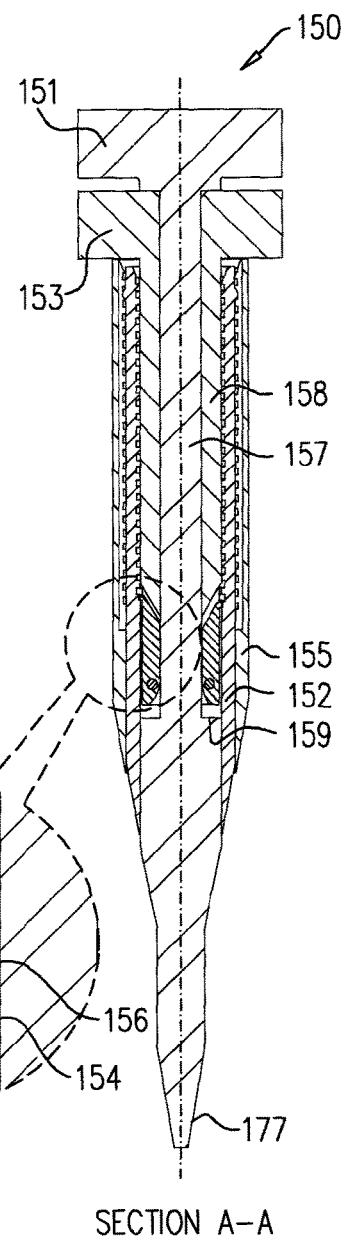
SECTION A-A

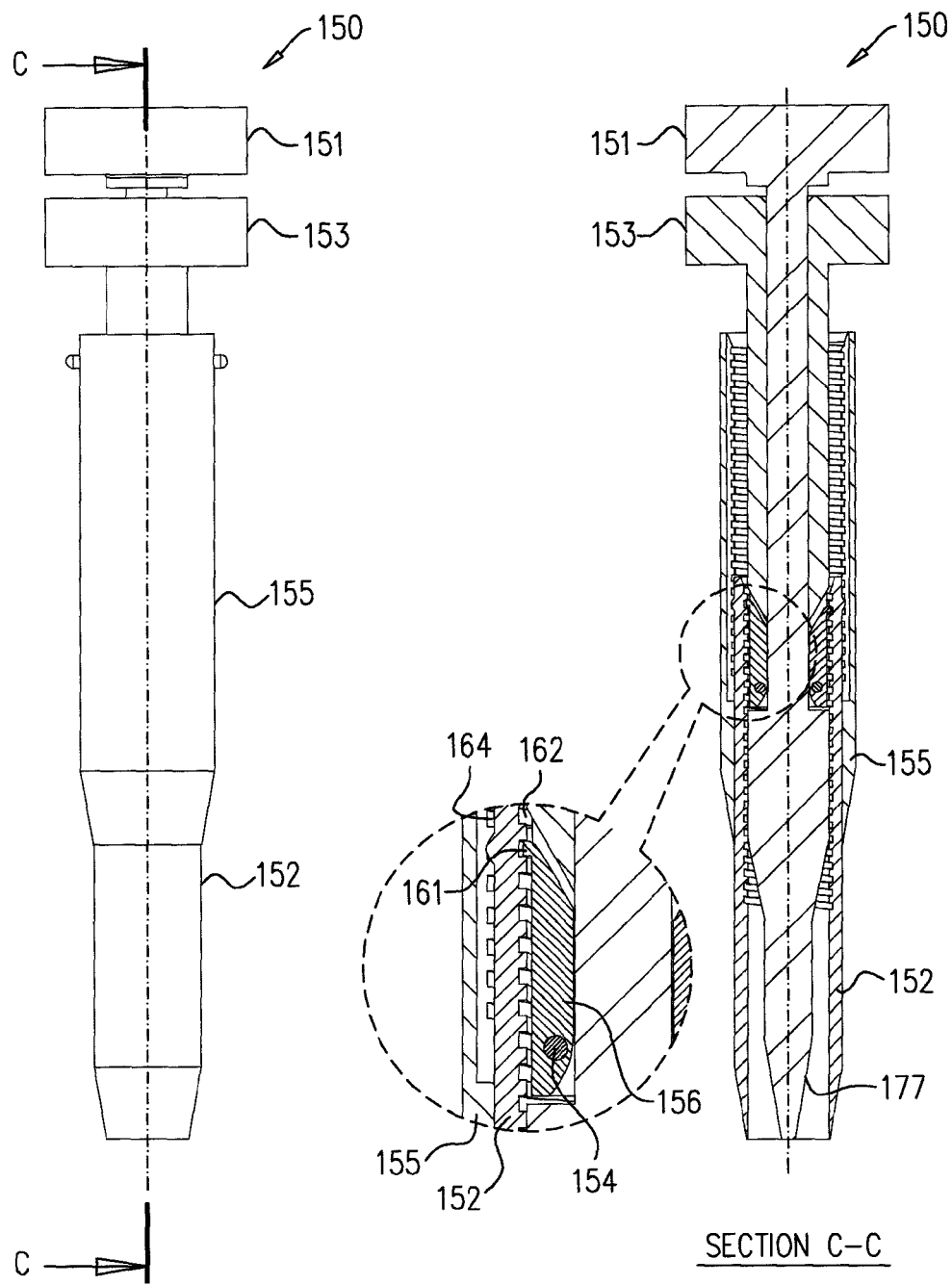

FIG. 27A
FIG. 27B
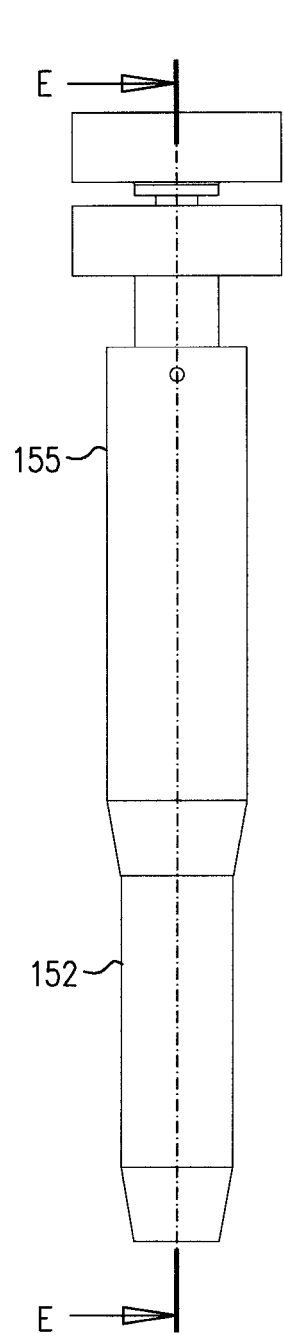
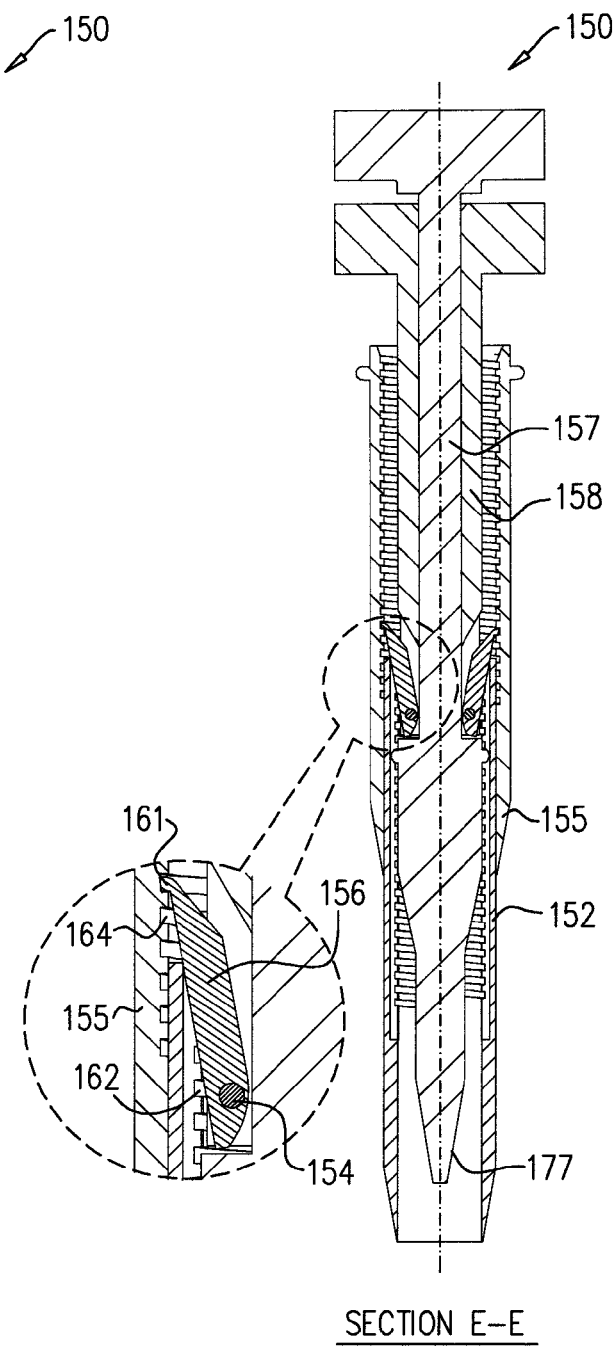
SECTION E-E

AUTOMATIC DILATOR

CROSS REFERENCE TO RELATED APPLICATIONS

This application is a national stage application under 35 U.S.C. § 371 of PCT Application No. PCT/IL2014/050845, having an international filing date of Sep. 22, 2014, which designated the U.S., and which claimed the benefits of and priority under 35 U.S.C. § 119(e) to U.S. Provisional Application Serial No. 61/880,953, filed on Sep. 22, 2013, entitled "Automatic Dilator."

FIELD OF THE INVENTION

The present invention relates to the field of dilators, especially sets of nested spreaders adapted for automatic insertion by means of mechanical motion conversion mechanisms.

BACKGROUND OF THE INVENTION

Sets of dilators are used in surgery in order to create an opening into a patient's body in order to gain access for such tasks as surgical or endoscopic procedures. They are particularly useful for minimally invasive surgical procedures, since the opening need be no larger than is required for the desired access. A dilator set comprises a series of dilator tubes of increasing diameter, each having a sharpened chamfered end so that they can be inserted with minimal tissue trauma, with the smallest diameter dilator tube inserted first, and the dilator tubes of increasing diameter inserted sequentially thereafter in order to enlarge the opening generated. Once the final and largest dilator tube has been inserted, the smaller inner ones can be removed, leaving a clear aperture for performing the desired surgical or endoscopic procedure.

Current sets of dilators are inserted manually one after the other by the surgeon, which is a time consuming procedure whose quality can be variable depending on the way the procedure is conducted. Some prior art dilator sets and the methods of using them are described in U.S. Pat. No. 4,772,266 to L. E. Groshong et al, for "Catheter Dilator/Sheath Assembly and Method" and in U.S. Pat. No. 5,792,044 to K. T. Foley et al, for "Devices and Methods for Percutaneous Surgery" and in U.S. Pat. No. 7,811,303 to T. W. Fallin et al., for "Bodily Tissue Dilation Systems and Methods" and in US Paten Application Publication No. 2013/0041398 to J. Goddard et al, for "Dilator".

A power driven dilator insertion system, such as using a power drive or a drill, or a robot could greatly speed up the insertion process. Additionally, the use of robotic procedures in computer aided surgery has raised the need for a dilator set, which can be inserted automatically into the patient's body, preferably without human intervention, other than perhaps initial alignment of the insertion position and direction.

There therefore exists a need for an automatically inserted dilator set which overcomes at least some of the disadvantages of prior art manual dilator sets.

The disclosures of each of the publications mentioned in this section and in other sections of the specification, are hereby incorporated by reference, each in its entirety.

SUMMARY

The present disclosure describes new exemplary automatic dilator devices for generating minimally invasive access apertures for performing surgical procedures or endoscopic surveillance. The automatic dilators have a common feature in that they comprise a plurality of spreader tubes nested one inside the other, which are deployed automatically by means of mechanical screw-based mechanisms which couple adjacent spreaders and ensure insertion of one spreader after the other distally into the patient's tissue. These coupled screw-based mechanisms are either (i) the mutual interaction of a rotating thread engaging element, such as one or more teeth, or a tab or tabs, or a section of thread form on the external surface of a first spreader element, with a helical thread formed on the inside surface of a second spreader element disposed external to the first spreader element which is constrained to move longitudinally as the thread engaging element rotates, or conversely, (ii) the mutual interaction of a rotating helical thread formed on the external surface of a first spreader element with a thread engaging element, such as one or more teeth, or a tab or tabs, or a section of opposing thread form, on the internal surface of a second spreader element disposed external to the first spreader element and constrained to move longitudinally as the helical driving thread rotates. A common feature is that the devices have a transfer mechanism that ensures sequential deployment of the spreaders, from the innermost to the outermost, by switching the thread engagement once the previous spreader has reached its required position, from one spreader to that immediately external to it.

According to a first exemplary implementation, each spreader interacts with the neighboring spreader, immediately external to it, by means of a short section of external threading or teeth or a tab or tabs on the external wall of the inner spreader meshed with an internal thread on the outer spreader. Rotation of the inner spreader while the outer spreader is prevented from rotating causes the outer spreader to move linearly relative to the rotating inner spreader, in much the same way as a nut, held so that it cannot rotate, rides down (or up) a screw as the screw is rotated. This combination of external and internal threading is applied to the nested spreader tubes of the device, and a rotatory mechanism is used to deploy one spreader tube after the other, by means of a continuous rotary motion. The dilator devices incorporate mechanisms which automatically transfer the longitudinal motion from an inner spreader to that immediately external to it, once the inner spreader has reached its intended depth of insertion. For an orthopedic access dilator, this mechanism can be the abutment of the spreader on the target bone, such that the prevention of further longitudinal motion of that spreader causes it to rotate together with the spreader immediately inwards of it, and thus to generate longitudinal motion in the spreader immediately external to it. In this way the automatic dilator device can be inserted into the patient by means of a continuous rotary motion in one direction, such as could be supplied by a surgical drill, or a robotic rotary drive.

According to a second implementation, each of the spreader tubes is individually rotated by means of a splined shaft running through either the spreader tube itself (in the case of the innermost spreader tube) or through a cover on the spreader tube, and engaging with internal spline grooves formed in that spreader tube or cover. A short proximal section of this splined shaft is formed without any splining, and the longitudinal position of the spreaders relative to this unsplined section is arranged such that all of the spreaders proximal to the spreader being deployed have their internal splined cover located at the unsplined section of the splined shaft, such that they do not rotate. When the spreader being deployed has reached its fully deployed position, its internal splined cover disengages from the distal end of the splined drive shaft, such that it no longer rotates, and the spline shaft with the drive assembly can be moved proximally so that the next outwardly disposed spreader tube is now engaged by the splined shaft and commences to turn and to move distally down the dilator device. In addition, a rotation blocking assembly is used to prevent rotation of all of the outer spreaders except that one which is driving the next spreader external to it, and this rotation blocker is moved proximally with the drive assembly to free that next spreader to enable it to rotate. This implementation also includes specific mechanical mechanisms, which will be fully expounded the Detailed Description section below, for defining which of the spreaders should be locked into position, and which should be enabled to rotate by the rotation of the splined tube. The operation regarding which spreaders should be locked into position and which be allowed to engage with the splined drive shaft has been described in the Detailed Description section below, by means of a hand held element such as a hand-grip, but it is to be understood that the operation of the device can equally well be performed using a clutch assembly in the case of a fully automatic insertion mechanism, such that an automatic sequential insertion of the spreader tubes is achieved, starting with the narrowest—the innermost one—and ending with the outermost one.

A third implementation, like the above-mentioned second implementation, has a series of concentric spreader tubes, each having an internal thread formed on its inside surface, but whose distal motion is generated by means of a set of spring-loaded hinged pawl elements mounted on the innermost element, each pawl element having an externally protruding tooth which meshes with the internal threads of the spreader tubes external to it, driving each of the spreader tubes distally into the tissue as the innermost element is rotated. As soon as a spreader tube reaches its distal deployed location, the external toothed protrusions on the hinged pawl elements slip off the end of the internal thread of that spreader, and being spring-loaded in an outward direction, now mesh with the internal thread on the next outwardly positioned spreader tube element at its distal end, and rotation of the inner element now begins to move that next outwardly positioned spreader tube longitudinally into the tissue. This implementation thus has the advantage over the second implementation that the successive insertion of the spreader tubes takes place automatically on continuous rotation of the innermost element, without the need for any intermediate operations to switch between successive spreaders.

There is thus provided in accordance with an exemplary implementation of the devices described in this disclosure, a an automatic dilator device, comprising:
(i) a plurality of concentric spreader tubes nested one inside the other, ranging from the innermost spreader tube to the outermost spreader tube, at least some of the spreader tubes comprising at least one protrusion on their outer wall and at least some of the spreader tubes having a helical thread formed on their inner wall, the at least one protrusion being adapted to engage the helical thread formed on the inner wall of the spreader tube disposed immediately external to it,
(ii) a rotation mechanism coupled to at least one of the spreader tube, such that when the rotation mechanism rotates a first spreader tube, a linear motion of a second spreader tube disposed immediately external to the first spreader tube is generated, and
(iii) a mechanical arrangement associated with at least the second spreader tube, such that when the second spreader tube reaches a predetermined deployed position, the mechanical arrangement transfers rotary motion of the rotation mechanism to the second spreader tube.

In such an automatic dilator device, the rotational mechanism may comprise a splined drive shaft, disposed axially through the innermost spreader tube, and adapted to mesh separately with an internally splined section associated with each of the spreader tubes, such that rotation of the splined shaft causes a spreader tube with which it is meshed to rotate.

Furthermore, the mechanical arrangement may comprise an axial motion mechanism that moves axially to selectively prevent or allow rotary motion of any of the spreader tubes.

In the above described splined shaft implementation, the splined shaft may have an unsplined section at its proximal end, and the plurality of concentric spreader tubes may be initially positioned and of such lengths that the unsplined section does not mesh with the internally splined section associated with those the spreader tubes which it is not desired to rotate. In such a case, the mechanical arrangement should comprise an axial motion mechanism which moves the splined shaft in a proximal direction such that its splined section meshes with the internally splined section associated with that spreader tube which it is desired to be rotated, which previously was disposed opposite the unsplined section.

According to a further implementation, the axial motion mechanism may comprise at least one axially moveable pin disposed off-axis to the spreader tubes, such that the axial motion inserts the at least one pin into an off-axis aperture in an end element of the spreader tube to selectively prevent or allow rotation of the spreader tube.

Additionally, in a splined shaft implementation of these automatic dilator devices, the splined drive shaft may have a length such that when a spreader tube reaches its predetermined deployed position, the internal splined section associated with the spreader tube slips of the end of the splined shaft and out of engagement with the splines, such that it is no longer rotated by the splined shaft.

In any of the above described implementations, the rotation mechanism may be adapted to deploy the plurality of concentric spreader tubes sequentially by rotation in one direction. Such rotation may be robotically generated.

Yet other implementations may involve a dilator device, comprising:
(i) a plurality of spreader tubes nested one inside the other, each of the inner ones of the spreader tubes comprising a section of external threading on its outer wall which is adapted to mesh with an internal thread on the inner wall of the spreader tube disposed immediately external to it and in close juxtaposition to it, such that rotation of a spreader tubes causes it to screw longitudinally into the spreader tube disposed immediately external to it,
(ii) a partially splined drive shaft disposed axially through the innermost spreader tube, and meshing with an internal splined section associated with each of the spreader tubes, and
(iii) a mechanism for axially moving the splined drive shaft relative to the spreader tubes, with its splined sections positioned to mesh sequentially with successively outwardly disposed spreader tubes, such that rotation of the partially splined drive shaft is adapted to cause the plurality of spreader tubes to deploy sequentially into a tissue of a patient.

Another example implementation can involve a dilator device, comprising:

(i) a plurality of concentrically nested spreader tubes, each having a section of internal threading on its inner wall, and (ii) a spiked rod with a rotator element, disposed within the innermost spreader tube, the rotator element comprising at its distal end at least one outwardly biased tooth element which meshes with the inner thread of the spreader tube immediately external to it, wherein rotation of the rotator element is adapted to cause the at least one outwardly biased tooth element to move the innermost spreader tube longitudinally in a distal direction, until the outwardly biased tooth element springs outwardly off the proximal end of the internal threading on the innermost spreader tube, and onto the internal threading on the next outwardly positioned spreader tube.

In such a dilator device, the outwardly biased tooth element may be a hinged pawl element incorporated into the rotator element, spring loaded such that it has an outwardly directed force acting on its end remote from the hinge, and may have an externally protruding tooth which meshes with the inner thread of the spreader tube immediately external to it.

Other implementations may further involve a dilator device, comprising:

(i) a plurality of concentrically nested spreader tubes, juxtaposed spreader tubes being mechanically linked by means of a helical thread form on one wall of one of the juxtaposed spreader tubes and at least one protrusion element engaging with the helical thread form on the facing wall of the second one of the juxtaposed spreader tubes, (ii) a rotation mechanism coupled to the inner one of the juxtaposed spreader tubes, such that when the rotation mechanism rotates the inner one of the juxtaposed spreader tube, a linear motion of the second one of the juxtaposed spreader tubes is generated in a direction parallel to the axis of the spreader tubes, and (iii) a motion transferring mechanism associated with at least the second one of the juxtaposed spreader tubes, such that when the second one of the juxtaposed spreader tubes reaches a predetermined deployed position, the motion transferring mechanism transfers the rotationary motion of the rotation mechanism to the second one of the juxtaposed spreader tubes.

In such a dilator device, the helical thread may be disposed on an inner wall of an outer one of the juxtaposed spreader tubes, and the at least one protrusion element disposed on an outer wall of the inner one of the juxtaposed spreader tubes. Alternatively, the helical thread may be disposed on an outer wall of an inner one of the juxtaposed spreader tubes, and the at least one protrusion element disposed on an inner wall of the outer one of the juxtaposed spreader tubes. In either of these situations, the at least one protrusion element may be any one of a section of thread form, a set of one or more teeth or a set of one or more tabs.

Yet other implementations perform a method of automatically inserting a dilator device into a subject, comprising:

(i) providing a plurality of concentric spreader tubes nested one inside the other, ranging from the innermost spreader tube to the outermost spreader tube, at least some of the spreader tubes comprising at least one protrusion on their outer wall and at least some of the spreader tubes having a helical thread formed on their inner wall, the at least one protrusion being engaging the helical thread formed on the inner wall of the spreader tube disposed immediately external to it, (ii) rotating at least one of the spreader tubes, such that a linear motion of a second spreader tube disposed adjacently outwards of the first spreader tube is generated, and (iii) providing a mechanical arrangement associated with the spreader tubes, such that when the at least one spreader tube reaches a predetermined deployed position, the mechanical arrangement transfers rotary motion to the second spreader tube disposed adjacently outwards of the first spreader tube. Such a method may comprise the step of providing further rotation until all of the plurality of concentric spreader tubes are deployed within the tissues of the subject.

Throughout this disclosure, the terms distal and proximal have their accepted meaning, distal referring to the direction into the patient's body, while proximal refers to the direction out of the patient's body and towards the applicator of the device. In the drawings of the present disclosure, since the device is shown entering a subject's body at the bottom section of the drawings, the proximal direction is shown upwards, and the distal direction, downwards.

Furthermore, although the mechanisms for switching between successive spreaders has been generally described in this disclosure using manually operated procedures, this is not meant to limit the invention, and it is to be understood that any of these mechanisms can equally well be performed using automated assemblies such as clutches and linear or rotary electromechanical actuators.

Additionally, although the dilator devices work equally well whether the continuous helical thread is on the inner or the outer surface of the spreaders, with the thread engaging elements incorporated accordingly to face the helical thread—with the exception of course of the innermost and outermost spreaders which need not have both thread and thread engaging elements—all of the examples described in this disclosure use a continuous helical thread form on the internal surfaces of the spreaders, and the thread engaging elements on the facing outer surfaces. It is to be understood, however, that this is not intended to limit the invention, and that either configuration is equally operable.

BRIEF DESCRIPTION OF THE DRAWINGS

The present invention will be understood and appreciated more fully from the following detailed description, taken in conjunction with the drawings in which:

FIG. 9 is a schematic assembly drawing of a second exemplary implementation of the automatic dilators described in this disclosure, also having internal helical threads engaging with external protrusions on the spreaders adapted to engage with the internal threads on the spreader immediately outwards of the protrusions, but differing from the dilator of FIGS. 1-8 in that the rotation and deployment of successive spreaders is controlled by a mechanical mechanism incorporating a splined shaft directing which spreader is operative in rotating to provide linear motion to that immediately outward of it;

FIGS. 10 to 23 illustrate schematically how, step-by-step, the automatic dilator shown in FIG. 9, can be deployed into a patient's body tissue;

FIGS. 25 to 27 illustrate schematically how, step-by-step, the automatic dilator shown in FIG. 25, can be deployed into a patient's body tissue

DETAILED DESCRIPTION

Reference is now made to FIGS. 1 to 8, which is a series of schematic illustrations of a first exemplary implementation of the automatic dilators described in this disclosure, showing the sequential stages of insertion of the dilator. The device comprises a number of hollow dilator tubes having incrementally increasing diameters, such that the dilator tubes fit sequentially within each other to form a nest of dilator tubes of increasing diameter, starting with the innermost and finishing with the outermost. The outer diameter of any one of the set is a sliding fit within the inner diameter of the next largest dilator tube, such that the set covers a complete range of diameters from the inner diameter of the innermost dilator to the outer diameter of the outermost dilator. Each of the dilator tubes has an internal screw thread over the whole length of its inner wall, and each of the dilator tubes, except the outermost one, has a section of screw thread formed on its outer wall at its proximal end. This section can be a short section covering typically only one or a few turns. Although the short screw thread section is used as the example for this implementation, it is to be understood that the devices are not intended to be so limited, but that the section of screw thread can be replaced by one or more teeth or tabs, or any other elements protruding from the outer wall, that can mate with the internal thread of the inner spreader. As a result of this combination, when a particular dilator tube is rotated, the short external screw thread section at its proximal end riding within the internal screw thread of the dilator tube immediately external to it, causes the dilator tube external to the rotated tube to move longitudinally relative to the position of the dilator tube being rotated, the relative direction of motion depending on the handedness of the threads generating the motion. Since it is conventional practice to positively activate rotary mechanical mechanisms by means of clockwise rotation of the actuating handle, and since the function of the auto-dilator is to drive the dilator tubes distally into the patient's tissues, the screw threads should be left-handed so that clockwise rotation of the actuating handle of the auto-dilator results in the desired distal motion of each successive outer tube.

In FIGS. 1 to 8, there is shown an exemplary auto dilator using the above described arrangement of internal and external threads, for use in orthopedic applications, though it is to be understood that this is merely one exemplary implementation, and that dilators for use in other applications can also be constructed in the same manner. The exemplary device shown in FIGS. 1 to 8 comprises five separate dilator tubes or spreaders, 12, 16, 17, 18, 19, though a different number can also be used.

Figure 1:
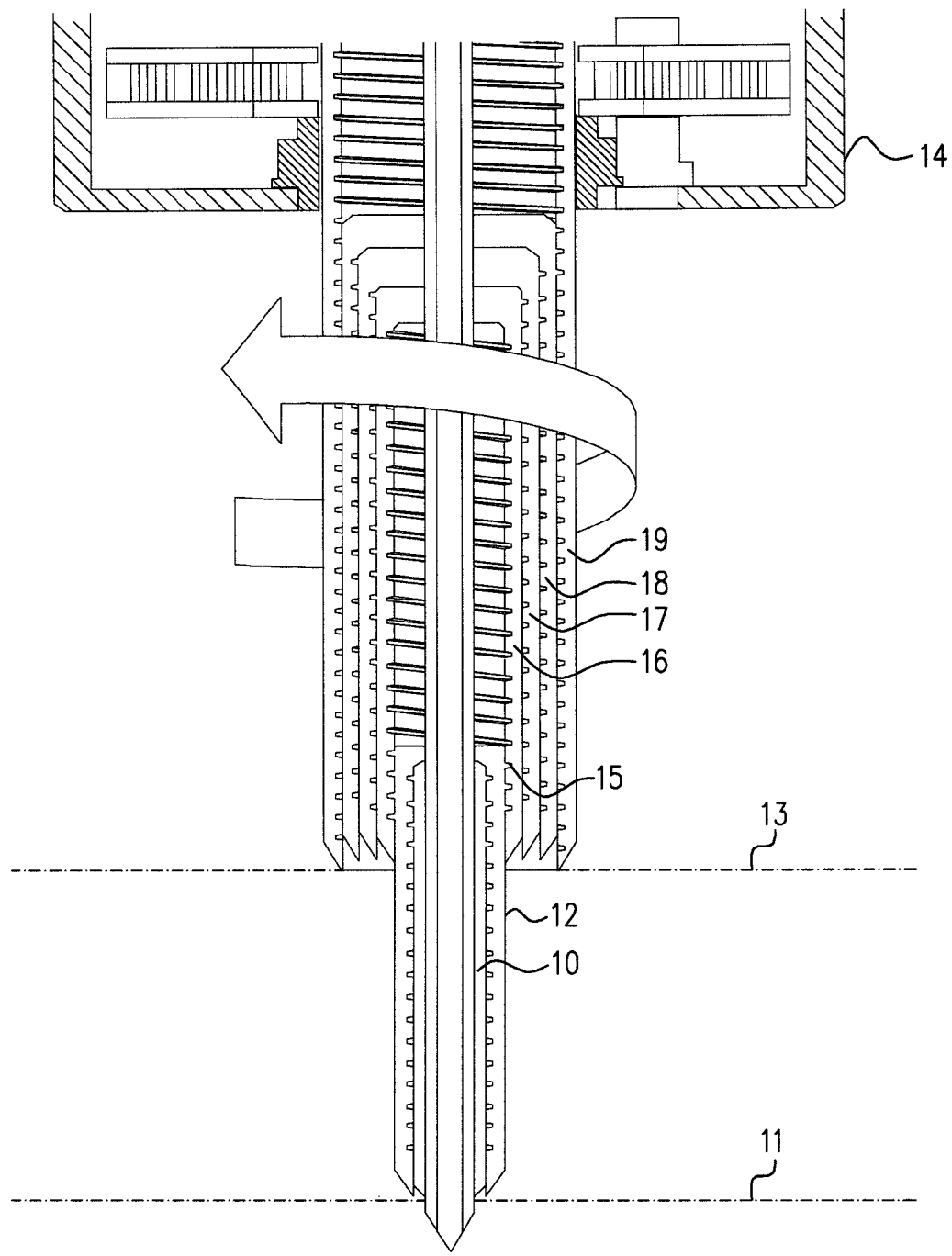
FIGS. 1 to 8 illustrate schematically a first exemplary auto dilator having a nest of spreaders with internal helical threads and opposing external protrusions on the spreaders external thereto to engage with the internal helical threads, rotation of the spreader with the internal helical thread causing the spreader with the external protrusions to move linearly, the series of figures showing the way in which the auto dilator is inserted into the patient's body tissue, step-by-step.

Reference is now made to FIG. 1, which shows the device after the first stage of insertion has been performed. The auto dilator is first positioned on the patient's skin 13, and, using the drive handle 14 at the proximal end of the device, the innermost element, a spiked rod 10, is driven into the subcutaneous tissue down to the bone surface 11, to which the auto dilator is intended to prepare an access passageway. A guide wire (not shown in the drawings) can be optionally used in order to define the position of insertion of the innermost element. The distal end of the spiked rod is adapted to make firm or penetrating contact with the bone surface 11. It may be fitted with a freely rotatable point, such that the rod can rotate freely even whilst its spiked point is firmly embedded in the bone, though this feature is not essential, since the spiked point may also be adapted to rotate within the bone surface without being dislodged from its intended position. The spiked rod has a number of external threads or protrusions 15 at its proximal end, so that as the rod is turned in a clockwise direction, the teeth of its external screw thread or the protrusions running within the groove of the internal thread of the spreader immediately external to it, causes that first spreader 12 to move distally down through the patient's skin 13, spreading the tissue as it proceeds. The chamfered distal end of the innermost spreader, with its leading edge sliding along the outer surface of the spiked rod, assists in enabling it to penetrate the patient's tissue with minimal damage to the tissue.

Figure 2:
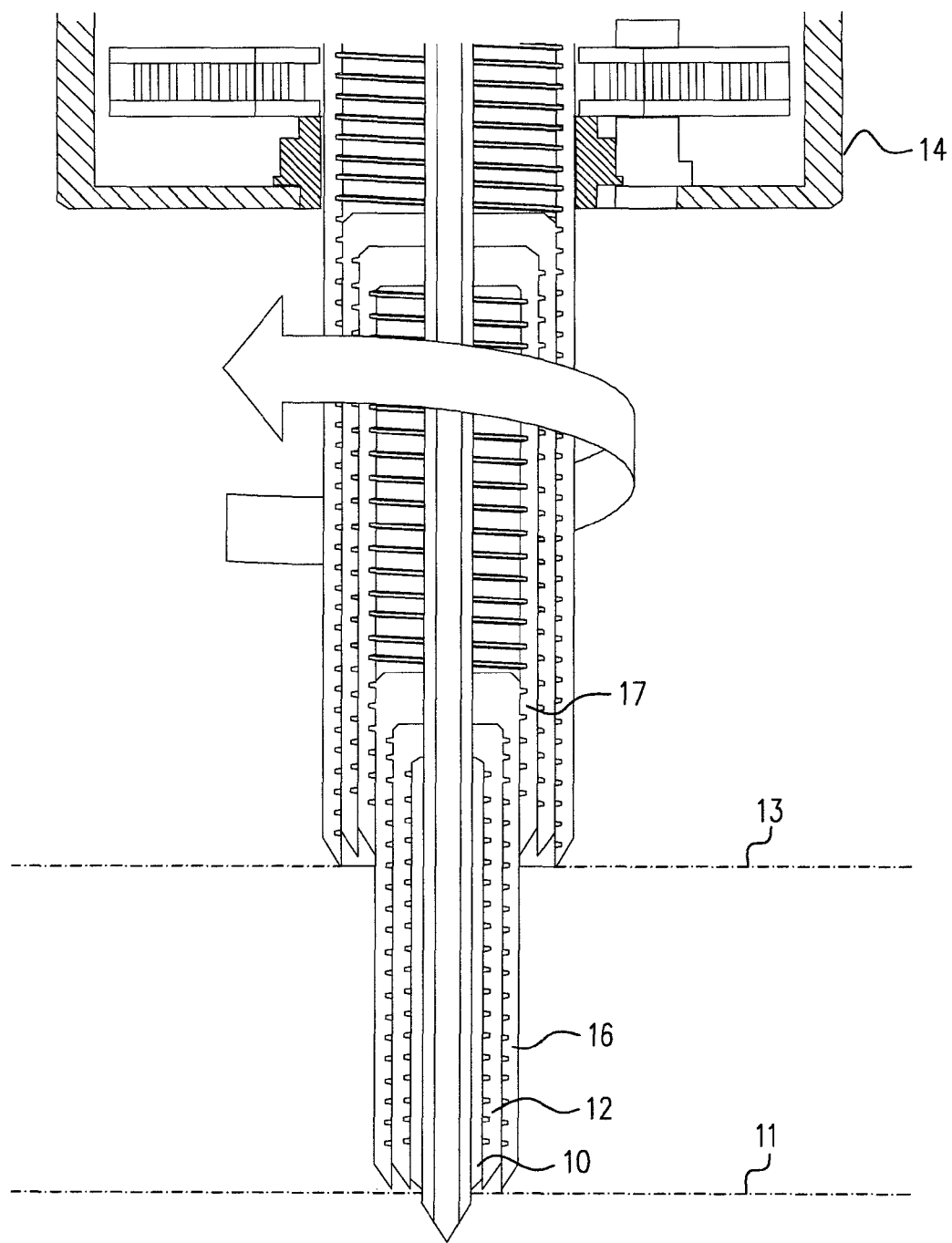
Figure 3:
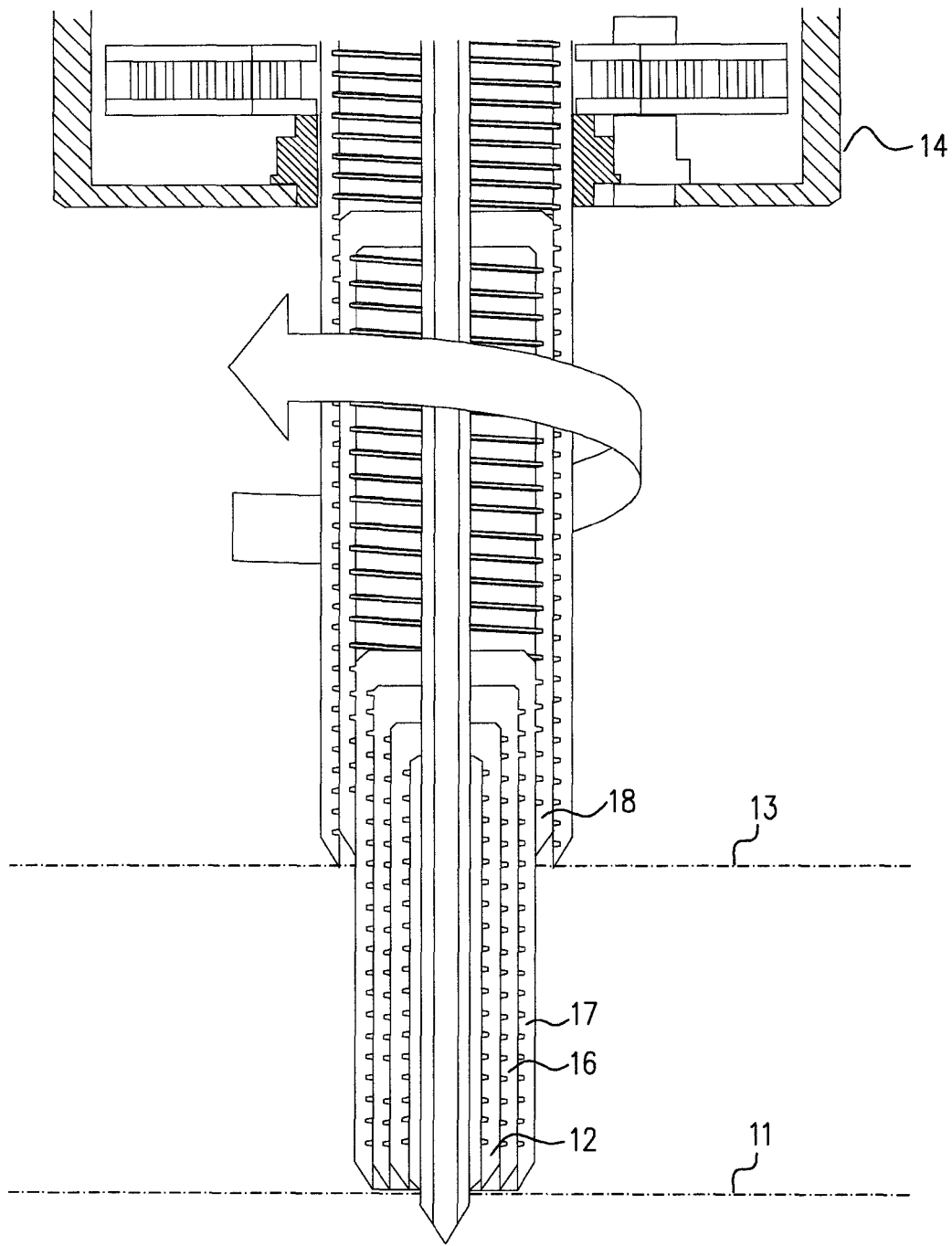
Figure 4:
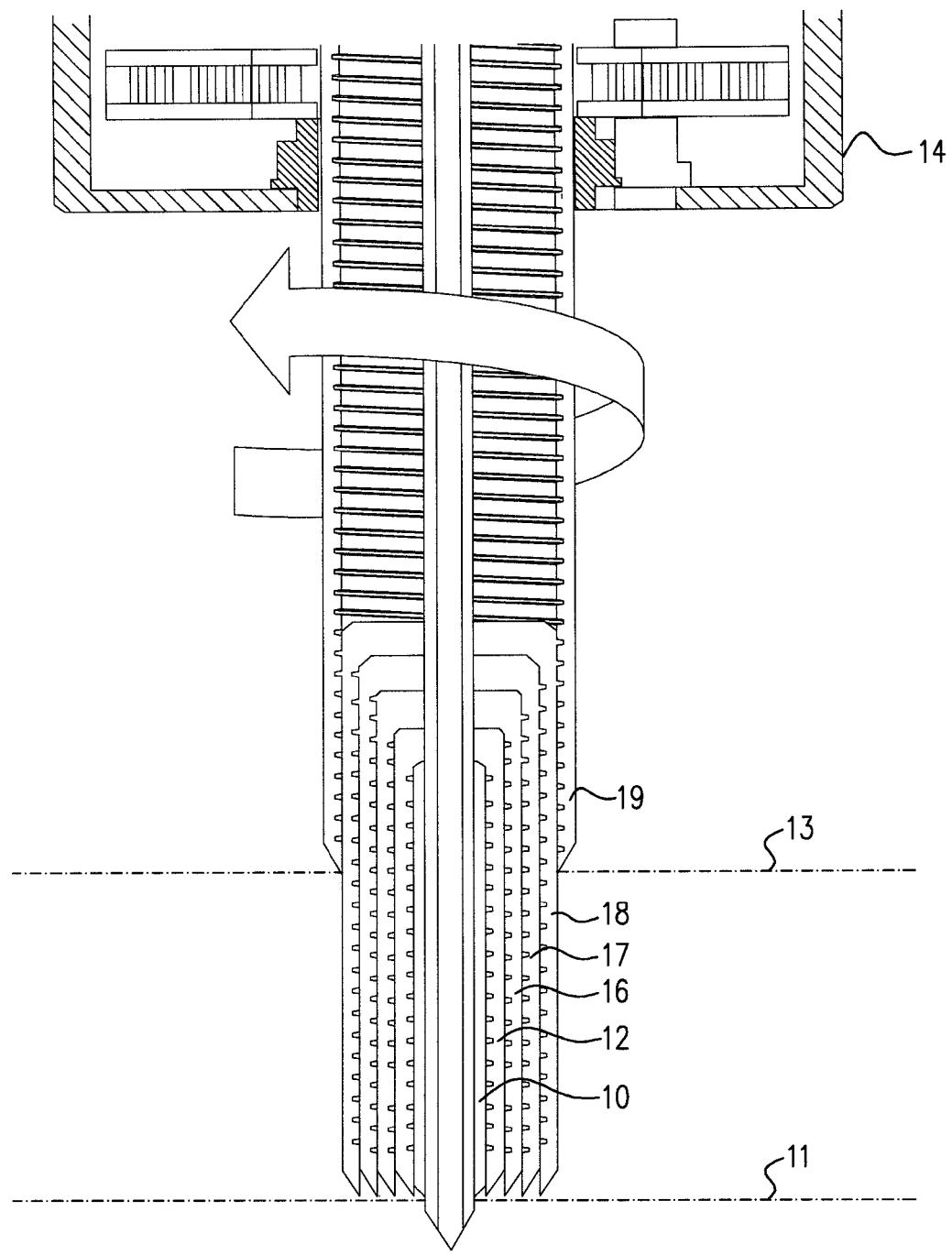

Once the innermost spreader 12 reaches its destination position against the bone surface 11, it can no longer move longitudinally into the patient's tissue, and since the spiked rod is continuing to turn, the innermost spreader 12 locks itself to the rotating spiked rod, and rotates itself in unison with the spiked rod. Once this action takes place, the commencement of the rotation of the few external threads 15 or the protrusions at the proximal end of the innermost spreader 12, which are meshed with the internal thread of the next spreader 16 (next in the sense of the radially outward direction from the innermost spreader), cause that next spreader 16 to move distally down the innermost spreader 12 by means of the screw action of the two meshing thread forms. This action continues until, as shown in FIG. 2, the next spreader 16 also reaches its destination at the surface of the bone 11, and its downward motion is stopped. At that point, it too begins to rotate in unison with the innermost spreader 12 and the spiked rod 10, and by the same action as it has itself previously undergone, using the few external threads or the protrusions at the proximal end, it begins to pull the next outermost spreader, the third spreader 17, downwards into the patient's tissue. This process continues until the third spreader 17 reaches its most distal point, as shown in FIG. 3, when the fourth spreader 18 begins its distal motion, and so on in FIGS. 4 and 5, in which the fourth spreader 18, and the fifth spreader 19 are shown to have been respectively completely inserted. The chamfered leading edge of each spreader is the leading edge, which is that which slides along the outer surface of the previously deployed spreader, thus providing a spreading effect to the tissue it is passing through, rather than a cutting effect.

Figure 5:
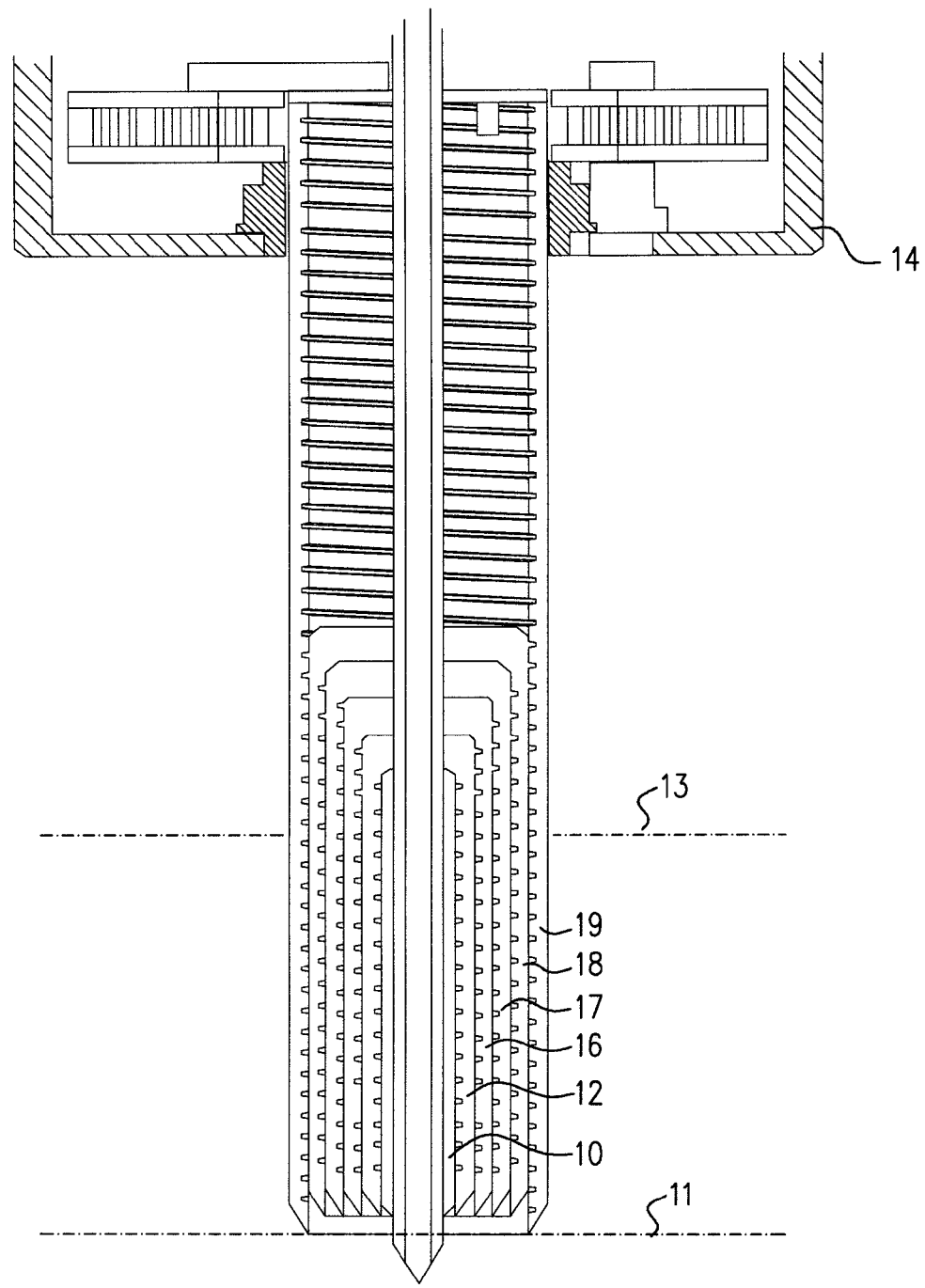

FIG. 5 now shows all five of the spreaders fully inserted, having spread the patient's tissue to the required diameter for the access aperture desired. As seen in FIG. 5, the outermost spreader 19—the fifth spreader in this example device—is longer than the previous, more internally disposed spreaders, and it is this outer spreader which constitutes the dilator tube, which will be used for providing access to the surgical site on the patient's bone. However, the dilator is not yet usable since its entire internal volume is taken up with the previous spreaders and the spiked rod. In order to utilize the dilator, it is necessary to remove all of the internal spreader tubes 12, 16, 17, 18, and the spiked rod 10, with their drive mechanism, leaving only the outermost spreader 19.

Figure 6:
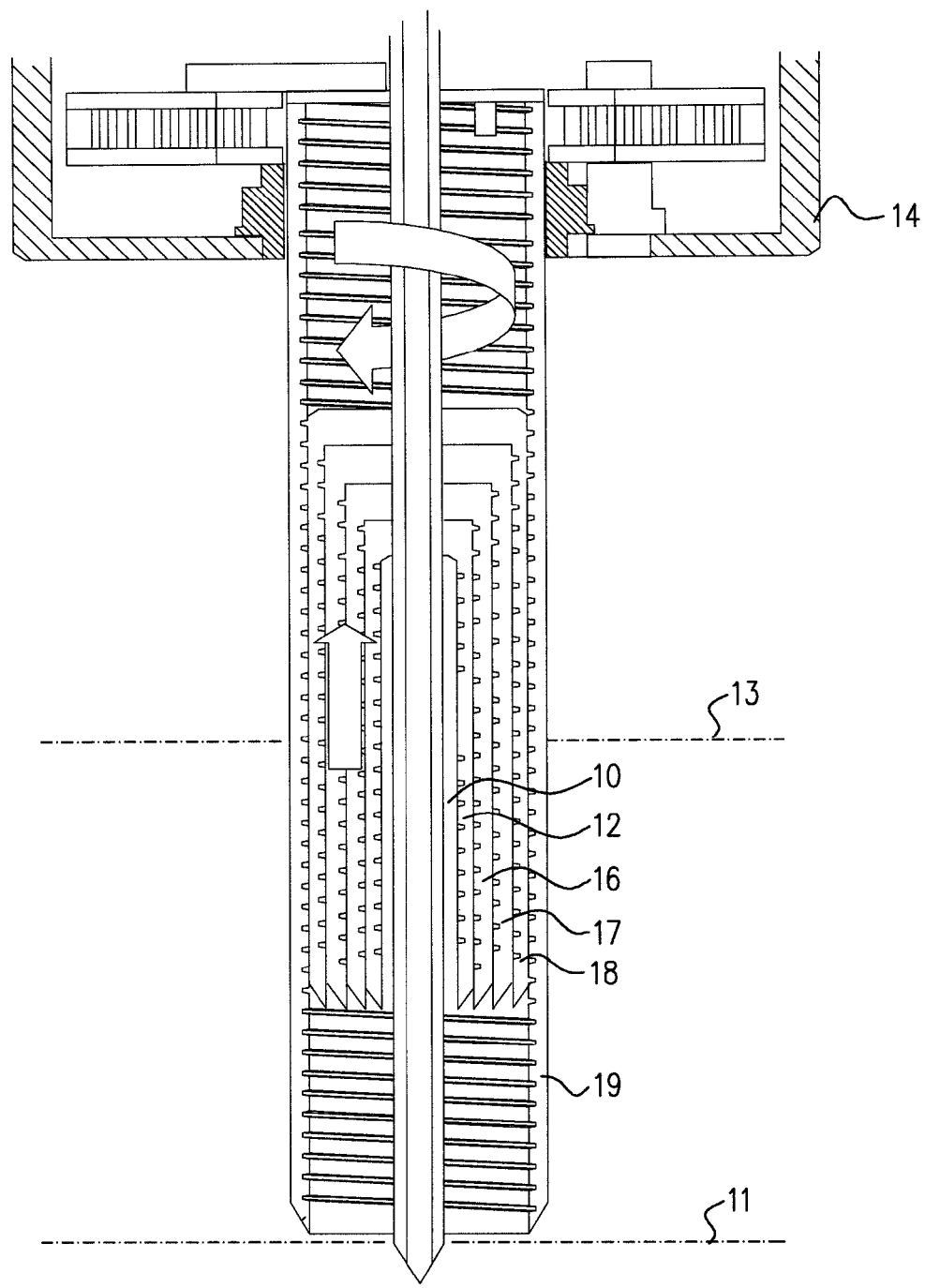
Figure 7:
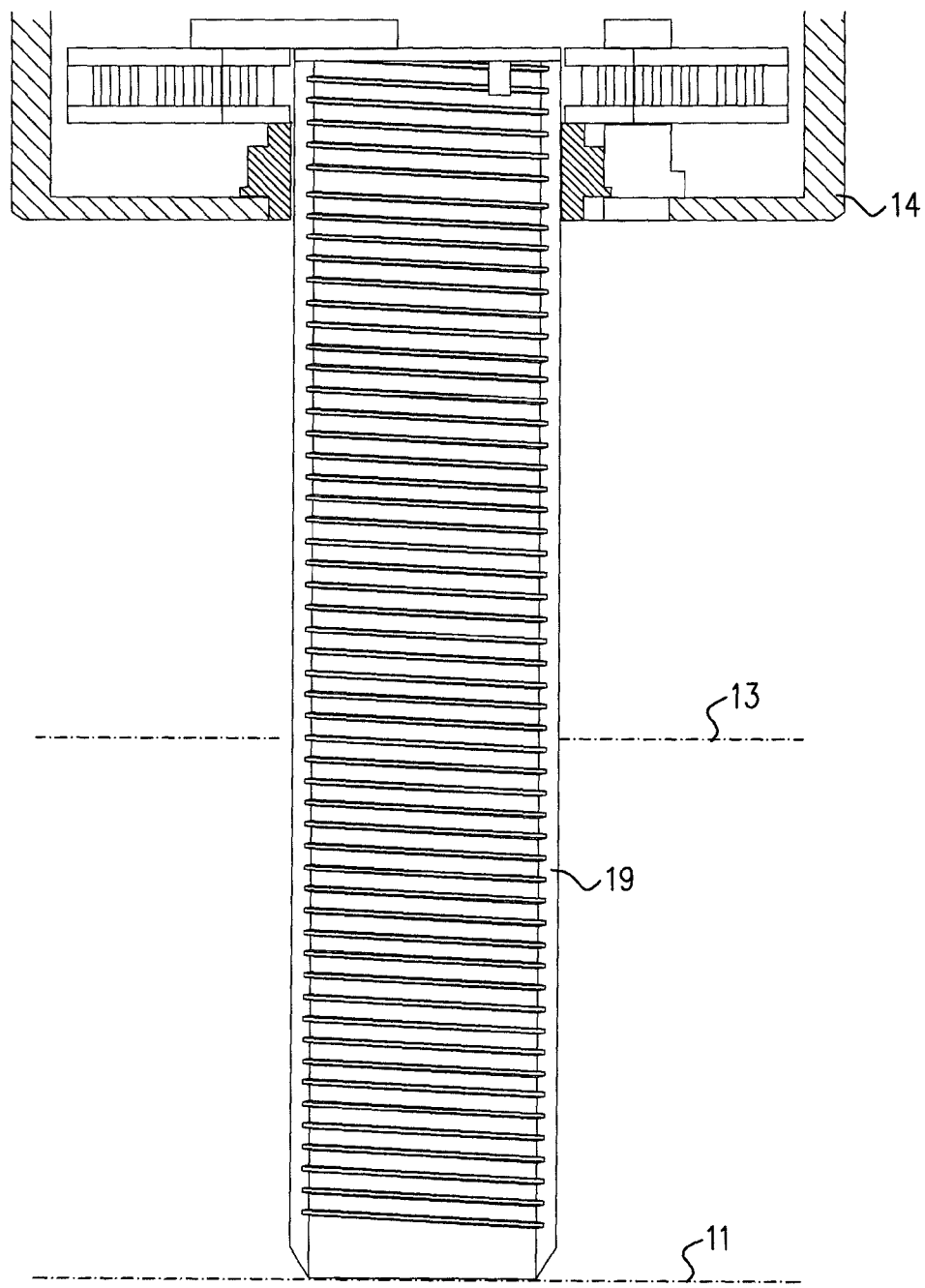
Figure 8:
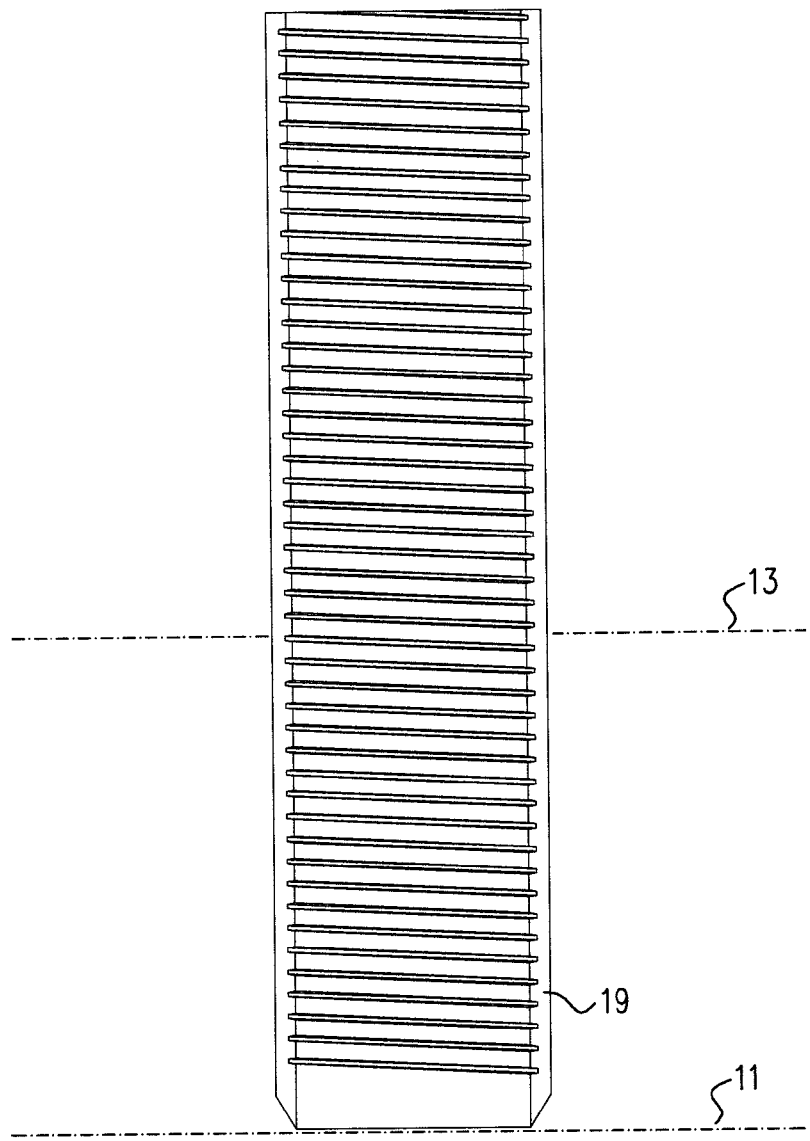

Reference is now made to FIG. 6 which illustrates how this is achieved. In FIG. 6, the actuating handle 14 is being rotated anticlockwise, and this action causes the nest of internal spreaders 12, 16, 17, 18, to rotate anticlockwise also, such that the outer screw thread on the fourth, penultimate spreader 18 meshing with the internal screw thread of the outermost spreader 19, causes the entire internal nest of spreaders to move proximally upwards through the outermost spreader 19, until they can be removed from the outermost spreader 19. The spiked rod 10 can then also be removed proximally, as shown in FIG. 7, followed by the activation handle and its mechanism 14, leaving just the outermost spreader tube 19, as shown in FIG. 8, which can then be utilized as the dilator tube for the surgical procedure to be undertaken.

Reference is now made to FIG. 9, which is a schematic assembly drawing of a second exemplary implementation of the automatic dilators described in this disclosure. FIG. 9 also includes a drawing of the assembled automatic dilator. This auto-dilator differs from that shown in FIGS. 1 to 8, in that it incorporates positive mechanical mechanisms for ensuring that each successive spreader reaches its destined position and is locked into place, and to ensure that the spreader deployment is performed in the correct sequential manner. In addition this implementation, more readily enables the auto dilator to be used in soft tissue without a bone structure to position its destination point accurately. As in the previous implementation, this auto dilator operates on the principle of a nested series of spreaders, each, except the innermost one, having an external thread form which engages with an internal thread section on the spreader immediately outward of it. However, unlike the previous implementation, in this model, each spreader is inserted longitudinally by a conventional screw action, in that as a particular spreader is rotated, it descends distally through the neighboring spreader immediately outward of it and into the patient's tissues, by conventional screw action of its external thread screwing into the internal thread of that outer spreader. In FIG. 9, there is shown an auto dilator with four nested spreaders, marked 91, 92, 93 and 94 in descending order of size. Spreader 91 has a cover 116, spreader 92 has a cover 96, and spreader 93 has a cover 95 all of which are fixed onto the proximal ends of the spreaders. The cover of innermost spreader 94 is already attached to the top end of spreader 94. A hollow splined rod 111 runs through all of these covers to the distal end of the spreaders, as shown in more detail in the blown-up drawing of the hollow splined rod running through cover 95. The proximal end of the hollow splined rod 111 is attached to a rotating handle 112, such that when handle 112 is rotated, the splined rod 111 rotates with it. A short section 100 of the proximal end of the splined rod has a reduced diameter, without splines. Inside of the hollow splined rod 111, there is a rod 98 having a spiked end, similar to that shown in the embodiment of FIGS. 1 to 8. At the distal end of the spiked rod 98, there is a pointed tip 120, to enable insertion of the spiked rod with minimal tissue damage, and which defines the position to which the auto dilator is to be inserted. In addition, there is a mechanism 89, 99, 110, at the distal end for locking the innermost spreader 94 to the spiked rod 98. The spiked rod 98 extends proximally to an operating handle 119 used for its insertion into the patient's tissue. Between the rotating handle 112 and the cover 116 of the outermost spreader 91, there is a collar-shaped cylindrical enclosure 114, with a raised shoulder at its proximal end, and the rotating handle 112 fits over this raised shoulder and is attached to the cylindrical enclosure 114 by means of locking screws 113 which fit under the shoulder after the rotating handle has been mounted over the shoulder, but which do not clamp the cylindrical enclosure, such that they allow the handle 112 to rotate freely relative to the cylindrical enclosure 114. The cylindrical enclosure 114 can be held stationary while the rotating handle 112 is rotated by means of a static handle 125 attached to the cylindrical enclosure. The cylindrical enclosure 114 has two spiral grooves 101 diametrically formed in its outer surface. A pair of positioning screws 117, one passing through each of the spiral grooves, is screwed into the top cover 116, and the position of the positioning screws 117 in the spiral grooves defines the longitudinal position of the cover 116 inside the collar shaped cylindrical enclosure 114. Three predefined positions are formed in the spiral grooves 101, defining three different heights of the cover 116 within the collar shaped enclosure 114, and hence also the longitudinal distance of the rotating handle 112 from the top of the spreader assembly, as defined by the cover 116 of the outermost spreader 91. Although in FIG. 9, the longitudinal height of the cover 116 inside the collar-shaped enclosure is shown as being determined by the position of two positioning screws 117 moving in two spiral slots 101, it is to be understood that this is only one method by which the height of the cover 116 can be adjusted and set, and that any other mechanism which achieves this object can equally well be used. Attached to the distal side of the rotating handle 112, there is a slip ring bearing 115, having two rotation prevention pins 118 extending in a distal direction into the covers of the spreaders. Further details of the component parts will now be expounded in the following explanation showing how the auto dilator operates.

Reference is now made to FIGS. 10 to 24 in conjunction with FIG. 9, to illustrate how this exemplary auto-dilator operates, and to explain the sequential stages of insertion of the spreaders. Each of FIGS. 10 to 24 illustrates a particular stage of insertion of the auto-dilator, generally in two views—a side elevation view and a cross sectional view showing the disposition of the internal parts.

In FIG. 10, the auto dilator is shown ready for insertion. In this drawing, it is observed that the length of the spreaders are linearly staggered, such that the outermost spreader 91 is the longest and the succeeding spreaders 92, 93, 94 are successively shorter, each difference in length being equal to the incremental change in height of the cover 116 between each preset position of the positioning screws 117. The differences in height are manifested at the top ends of the spreaders, such that the rotation prevention pins 118 protrude different lengths into the successive spreaders. Additionally, the unsplined top section 100 of the splined rod 111 is of such a length that in the initial undeployed situation of FIG. 10, the splines only mesh with the innermost spreader 94, which is the spreader with the most distally positioned proximal end.

Figure 11A:
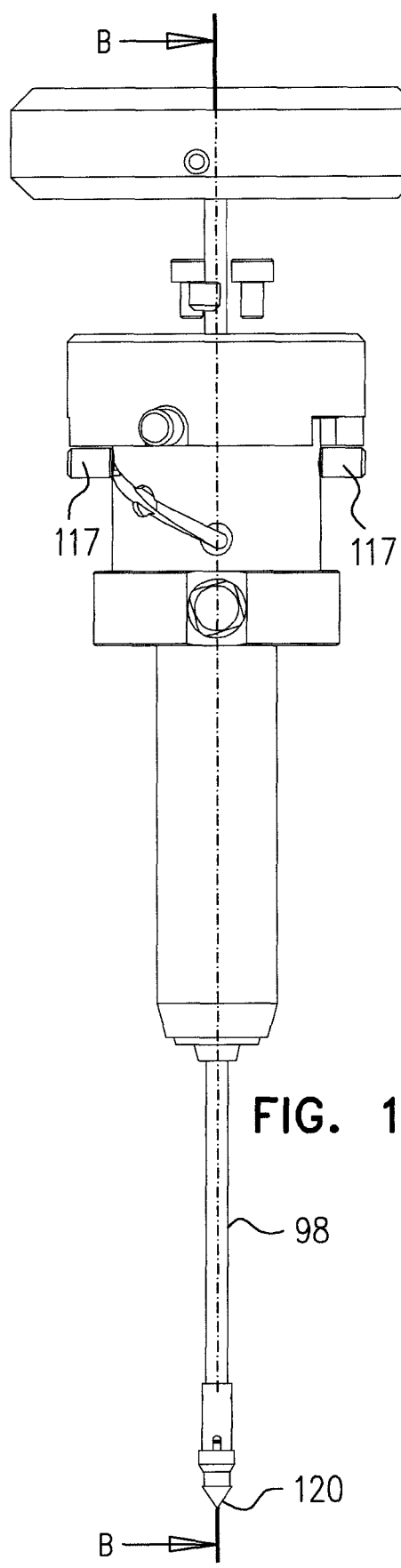
Figure 11B:
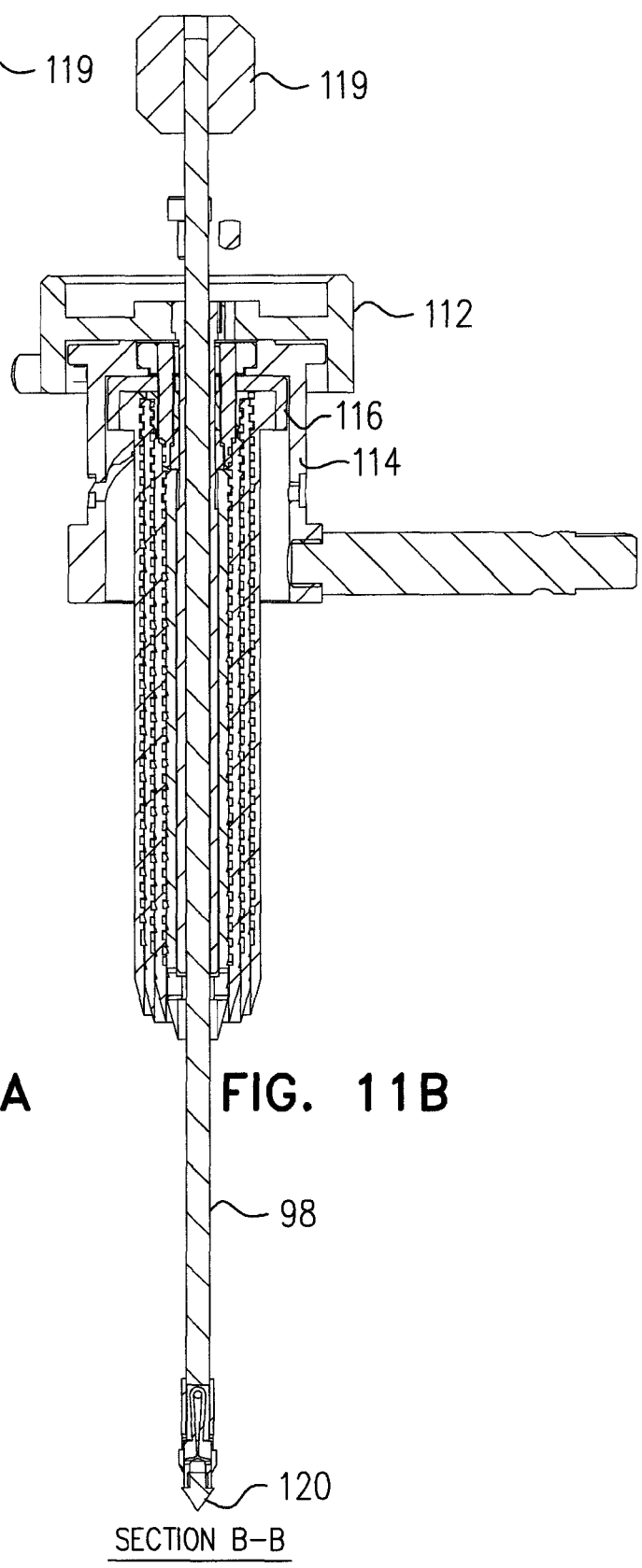

In FIG. 11, there is shown insertion of the spiked rod 98 into the patient's tissue by means of pressure on, and also optionally rotation of the handle 119. The other details are as numbered in FIG. 10, and are not repeated in this drawing or the following ones, if not necessary to explain operation of the auto-dilator.

Figure 12A:
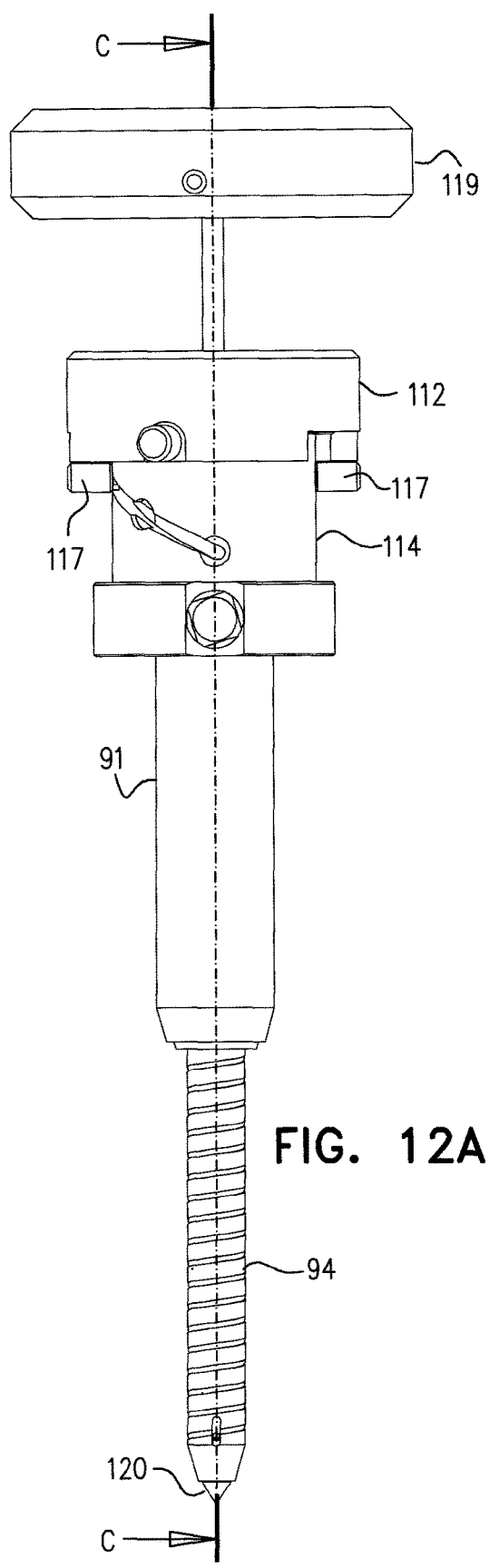
Figure 12B:
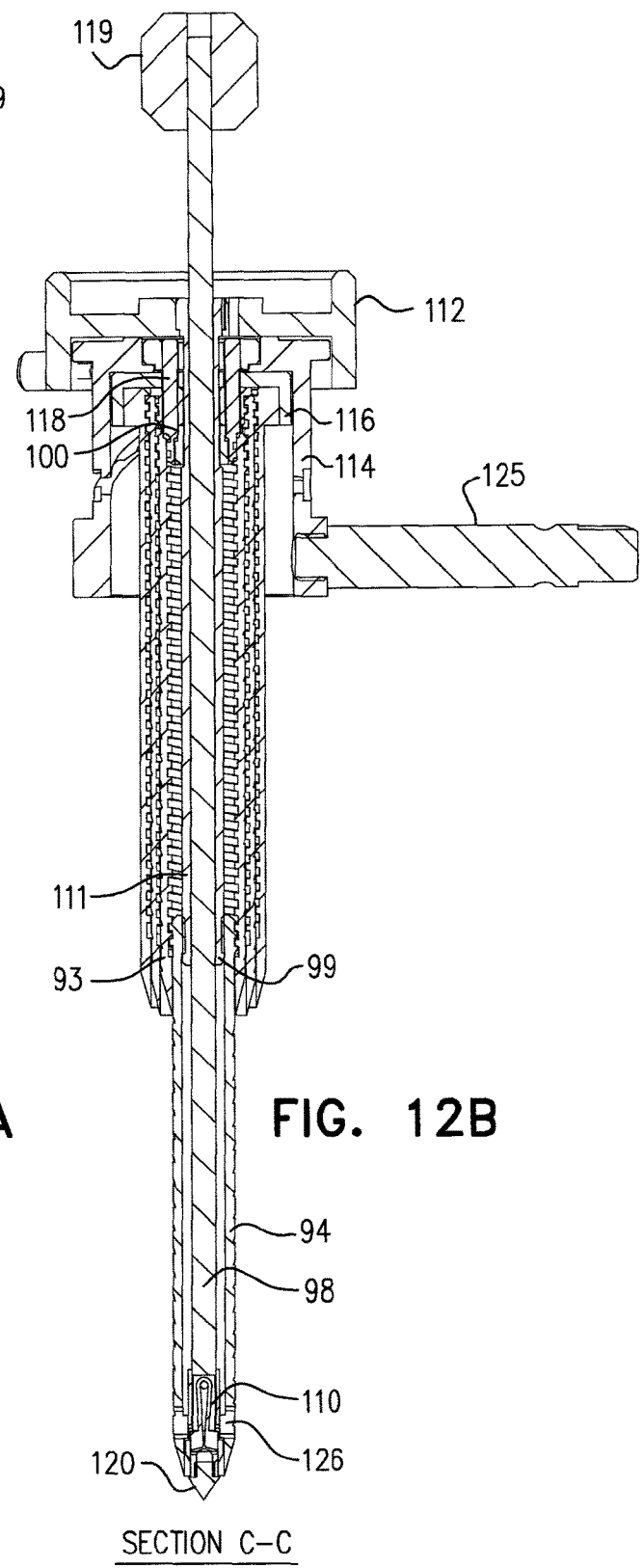

In FIG. 12, insertion of the innermost spreader 94 is commenced by the rotation of the handle 112, such that the splined rod 111 rotates with it. Because of the dense detail of the assembled dilator drawings in FIGS. 12 to 24, reference should also be made to the assembly drawing of FIG. 9 to see clearly how the insertion procedure is executed. In FIG. 12, as the splined rod rotates, its splines, being meshed with the inner splines in the cap of the innermost spreader 94, also cause the innermost spreader 94 to rotate. The meshing of the outer thread of the innermost spreader 94 with the internal thread of spreader 93, its immediately neighboring outwardly positioned spreader, causes spreader 94 to screw downwards into the patient's tissue. Because of the clear unsplined top section 100 of the splined rod 111, rotation of the splined rod does not have any effect on the other spreaders, which are not rotated by rotation of the splined rod. The cylindrical enclosure 114 and all of the remaining components attached thereto are kept from rotating by means of the handle 125. Furthermore, the rotation prevention pins 118 attached to the rotating handle 112, project into covers 95 and 96 of spreaders 93 and 92 respectively, holding them static. When spreader 94 reaches its bottommost position, as shown in FIG. 13, its distal end pushes an annular locking ring 99 (see FIG. 9) in a distal direction, thereby releasing the locking fingers 89 of the locking spring 110, shaped like an omega, which can then expand in an output direction into an internal groove 126 formed on the end of innermost spreader 94. This action locks innermost spreader 94 to the spiked rod 98, which, since it is held in a static position within the patient's tissue by means of handle 119, also clamps innermost spreader 94 into position at its most distal position, with its end at the target position to which the auto-dilator is to be deployed in the patient's tissue. Furthermore, the innermost spreader 94 is also prevented from rotating further by means of this clamping mechanism. At this point, the innermost spreader 94 has thus been deployed into its correct within the patient's tissue. The length of the splines on the shaft 111 are such that when the spreader 94 reaches its completely deployed position, its cap 99 has just slipped off the end of the splines on shaft 111, which can therefore no longer continue to rotate spreader 94.

Reference is now made to FIG. 14, which illustrates the following step, in which the next spreader 93, in an outward direction, must now be deployed. In order to do so, two actions must be performed:
(i) Firstly, the splined drive shaft 111 must be released from engagement with innermost spreader 94, and must be engaged with the next outer spreader 93.
(ii) Secondly, the rotation prevention pins 118 must be retracted from spreader 93 to enable it to be turned freely by the splined driver shaft 111.

Both of these results are achieved by the single action of freeing the positioning screws 117 in the cylindrical enclosure 114, and by moving the enclosure 114 together with its attached rotary handle 112 in a proximal direction until the next screw position is reached, and by retightening the positioning screws 117 in that position, as can be observed by comparison of the position of the screws 117 in the elevation drawings of FIG. 13 (positioning screws 117 in top position) and FIG. 14 (positioning screws 117 in middle position).

Reference to the sectional drawing of FIG. 14 now shows the operative result of this action. Both the splined drive shaft 111 and the pin assembly 115 are attached to the rotary handle 112. Therefore, the motion of the rotary handle 112 in the proximal direction, away from the nest of spreader tubes partially inserted into the patient's tissue, results in the motion proximally of the splined drive shaft 111 and the pin assembly 115 with its rotation prevention pins 118 away from the spreader tube assembly, as can be readily seen by the enlarged space 127 between the cover 116 of the outermost spreader tube 91 and the roof of the cylindrical enclosure 114 to which the rotary handle 112 is attached. This action essentially enables the two desired results mentioned above:
(i) The splined drive shaft moves proximally by an amount which releases its distal end from engagement with the internal spline grooves of the innermost spreader tube 94, and at the same time, the proximal end of the splines moves up and now engages the cover 95 of the second spreader tube 93, where previously, in FIG. 13, that cover was positioned longitudinally in the unsplined top section of the splined shaft, so that it did not rotate with rotation of the splines.
(ii) The rotation prevention pins 118 move proximally by an amount which frees their insertion into the cover 95 of spreader 93, such that spreader 93 is no longer prevented from rotating, and can now be turned freely by the splined driver shaft 111.

Reference is now made to FIG. 15, which illustrates the result of rotation of handle 112, such that the splined rod 111 rotates with it and consequently also the second to innermost spreader 93. Its external threads propel it down the internal thread system of the next outward spreader 92, further spreading the patient's tissues, until it reaches its distal target position next to the innermost spreader, where the splines on the splined drive shaft 111 slip out of the internal splined grooves in its cover 95, and thus no longer propel it distally downwards.

Figure 16A:
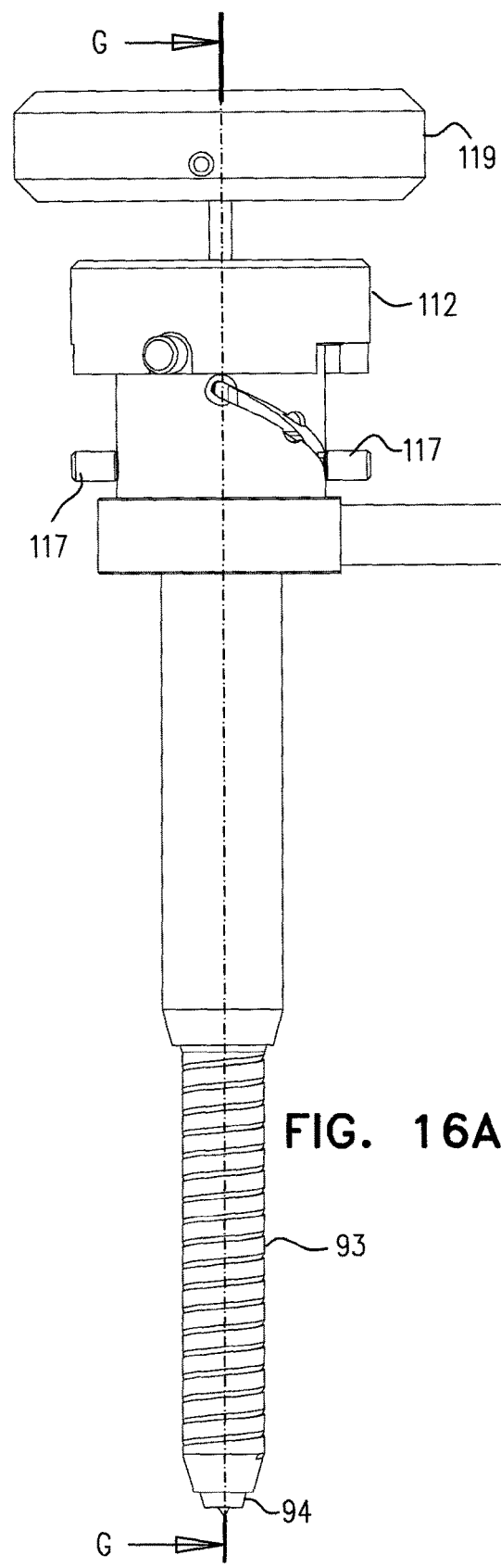
Figure 16B:
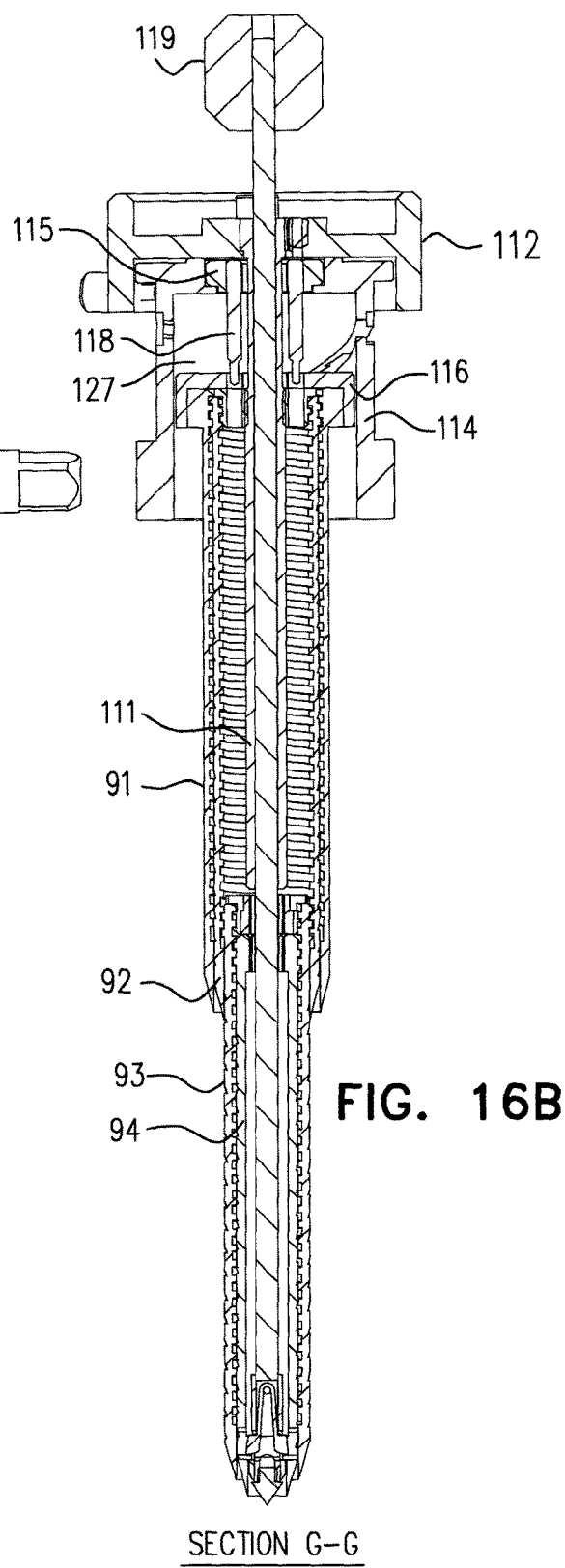

At this point both of the innermost spreaders are deployed and reference is now made to FIG. 16, which illustrates how the device is adjusted again, so that the third from the innermost spreaders 92 can now be deployed. This is done in a similar manner to that shown in FIG. 14, but this time, the positioning screws 117 are shifted from the middle position in the cylindrical enclosure to the most distal position. The height of space 127 then increases even more from its height when pins 117 were in the intermediate position. Pins 118 now only prevent cover 116 of outer spreader 91 from rotating.

Figure 17A:
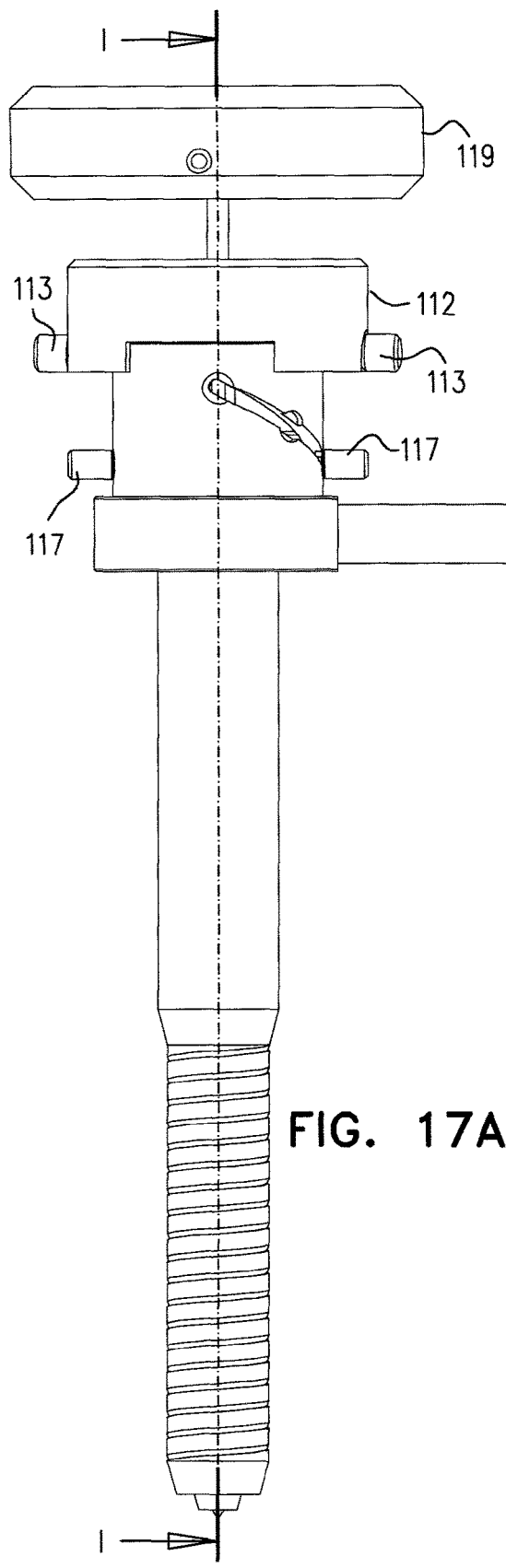
Figure 17B:
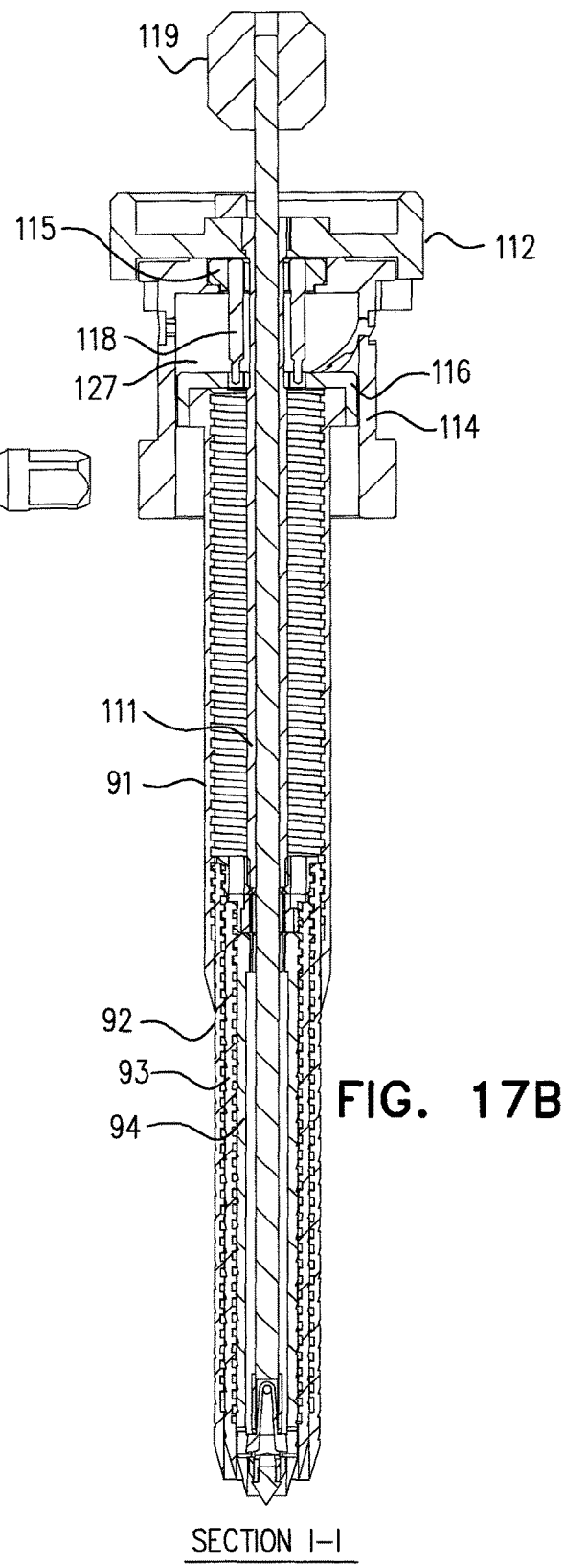

In this position, the proximal motion of the splined drive shaft 111 and the rotation prevention pin assembly 115 and its pins 118 away from the spreader tube assembly causes the splined drive shaft to release from engagement with the internal spline grooves of the cover 95 of spreader tube 93, and to engage with the spline grooves of cover 96 of spreader tube 92, and in addition, causes the rotation prevention pins 118 to move proximally to free their insertion in the cover 96 of spreader 92, such that spreader 92 is no longer prevented from rotating, and can now be turned freely by the splined driver shaft 111. Rotation of handle 112 can then be used to deploy the third innermost spreader 92, further spreading the patient's tissue until it reaches the target destination alongside the first two spreaders, 93, 94. This position is shown in FIG. 17, where the presence is shown of the locking screws 113, which lock the rotating handle 112 to the cylindrical enclosure body 114.

Figure 18A:
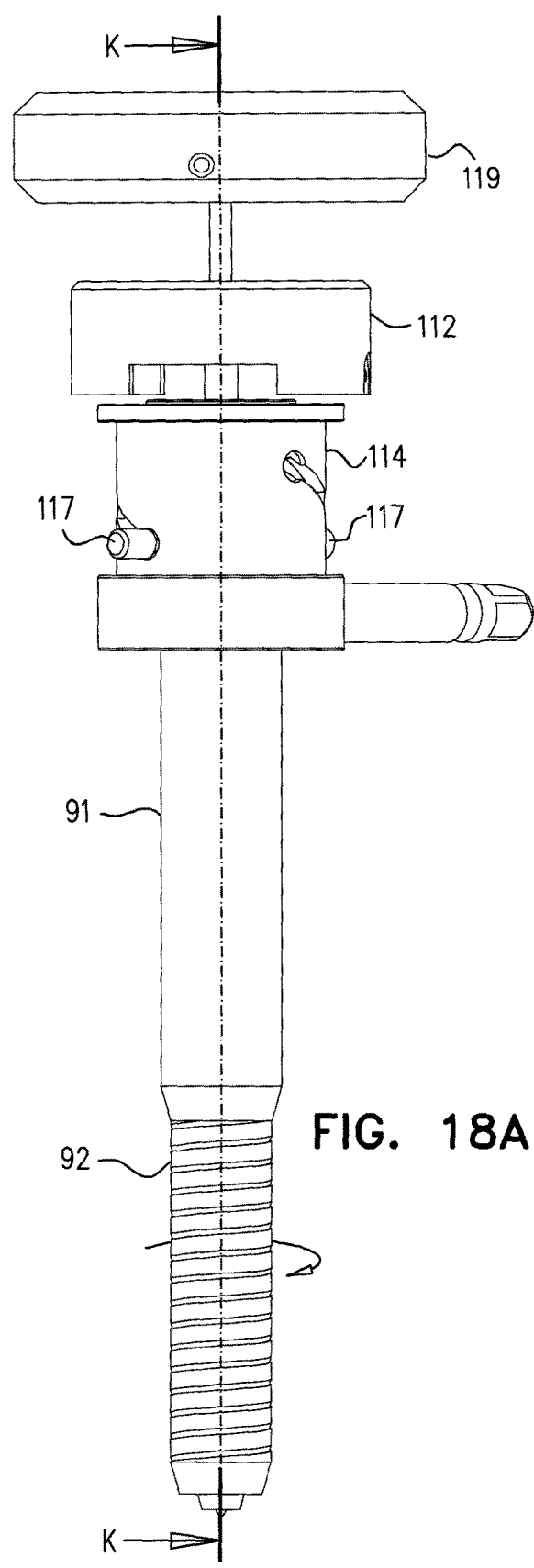
Figure 18B:
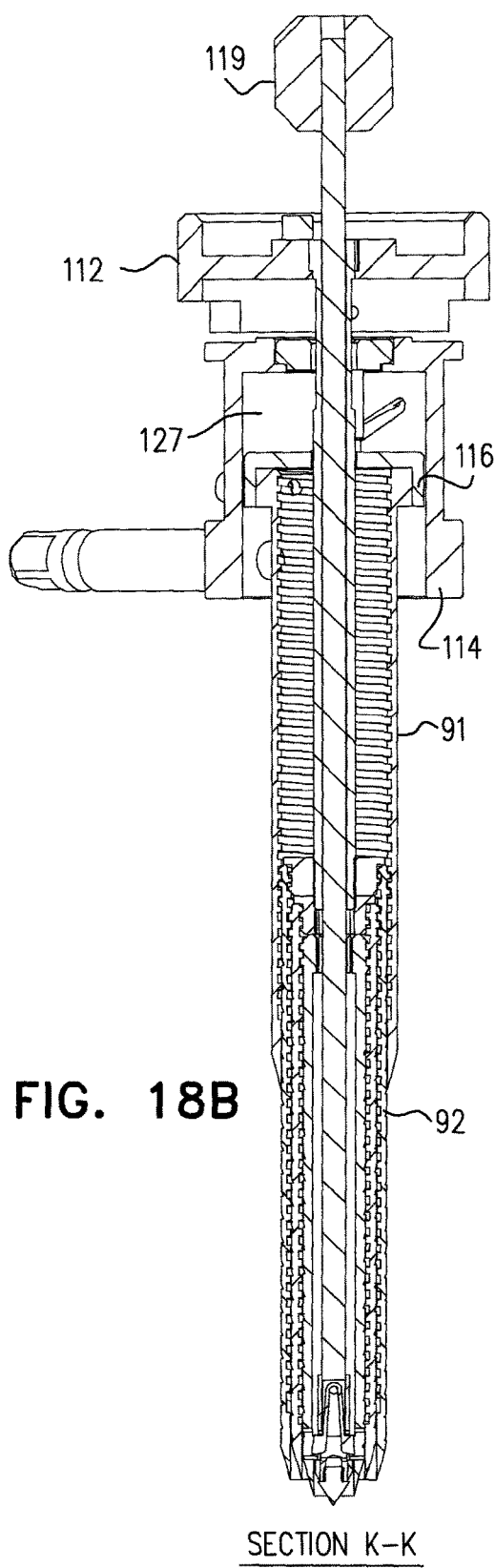

Reference is now made to FIG. 18 to illustrate the deployment of the final and outermost spreader 91. Since the outer spreader 91 cannot be inserted by screwing into any other element external to it, a somewhat different technique must be adopted. The locking screws 113 used to attach the rotating handle 112 to the cylindrical enclosure body 114 are removed, enabling the rotating handle 112 to be physically disconnected from the cylindrical enclosure body 114. At this point, rotation of the cylindrical enclosure body 114 attached to the cover 116 of the outermost spreader 91, enables the outermost spreader 91 to be screwed distally over the external threads of the penultimate spreader 92, until it reaches its fully deployed position over the first three spreaders. A fine external thread on the outer surface of the outer spreader, and even on the outer surfaces of the other spreaders, may facilitate their insertion into the tissue of the subject, though such outer threads play no part in the dynamics of the insertion mechanism of the device.

Figure 19A:
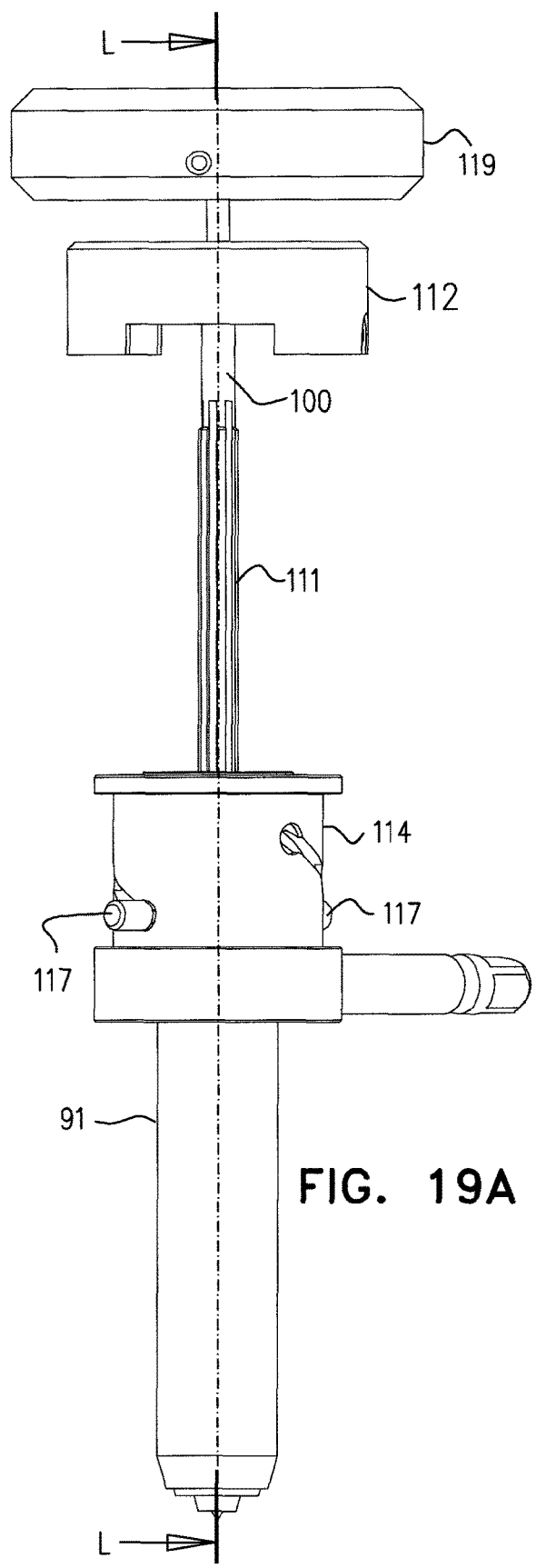
Figure 19B:
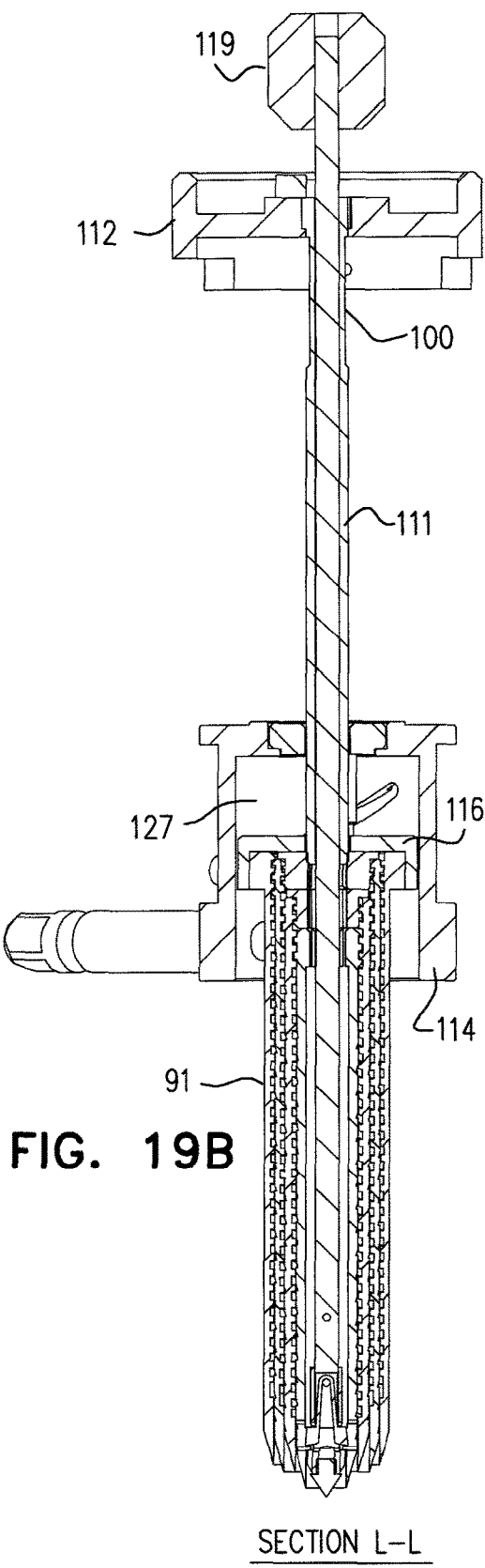

Reference is now made to FIG. 19, which shows the outer spreader 91 fully deployed, and the rotating handle 112 at the top end of the splined shaft 111 on the unsplined part 100, while the cylindrical enclosure body 114 has been screwed down with the outermost spreader towards the entry point of the device on the patient's skin. All that remains now in order to leave the outermost spreader 91 lodged in the patient's tissues, is for the nest of the three innermost spreaders 92, 93, 94, to be removed from inside the outermost spreader 91, together with the drive spline shaft, the spiked rod, and the cylindrical enclosure body 114. This procedure is now shown in FIGS. 20 to 23.

Figure 20A:
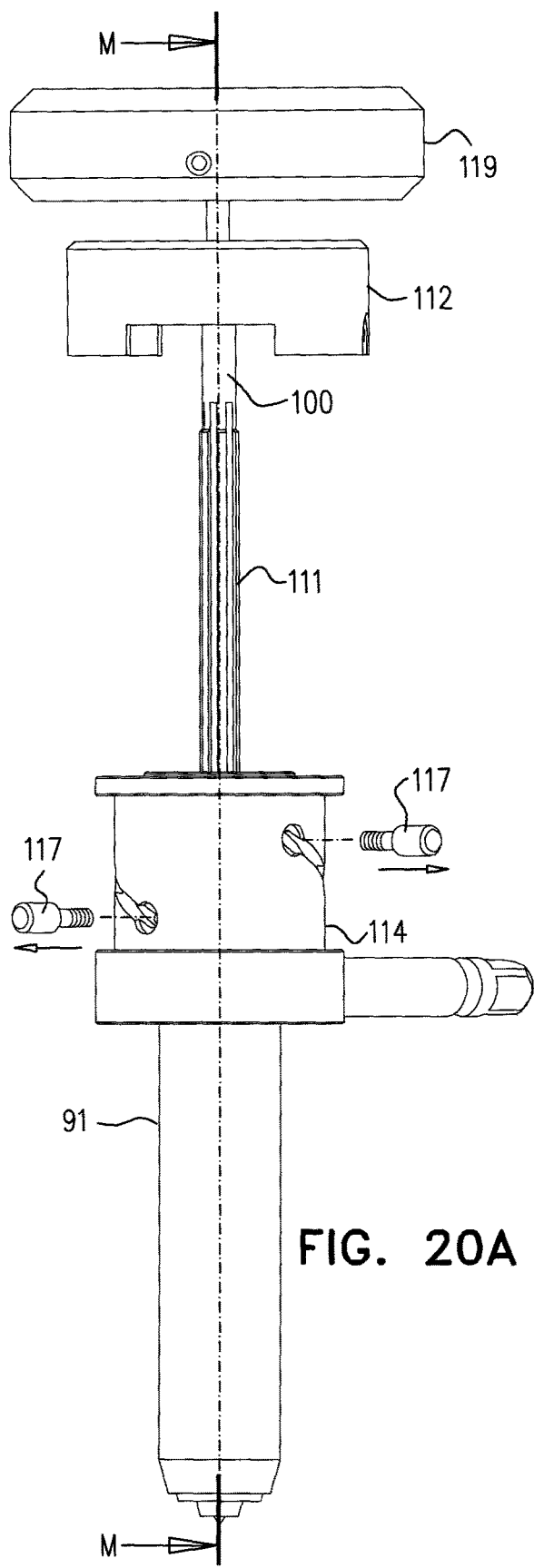
Figure 20B:
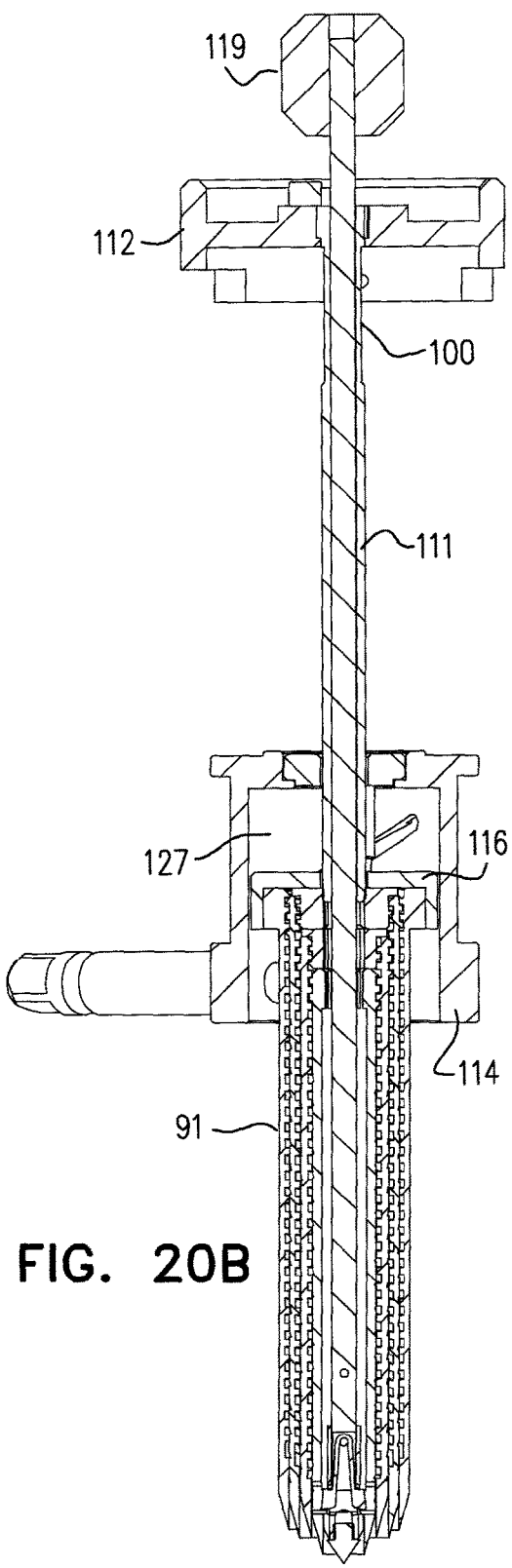
Figure 21A:
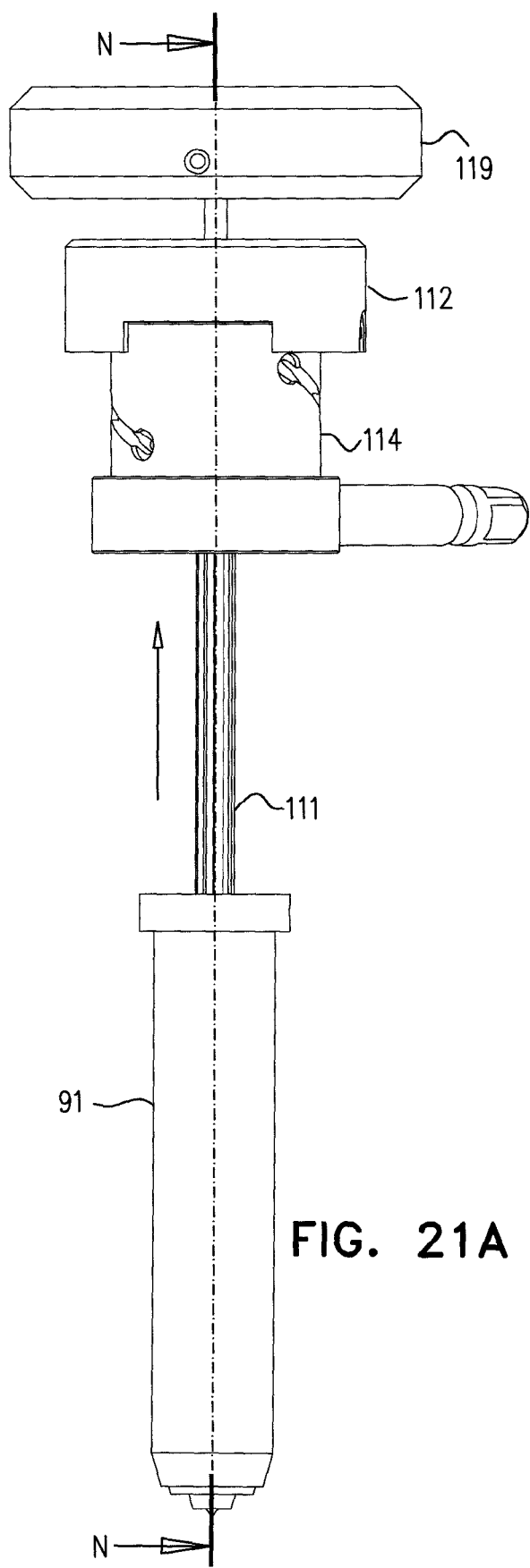
Figure 21B:
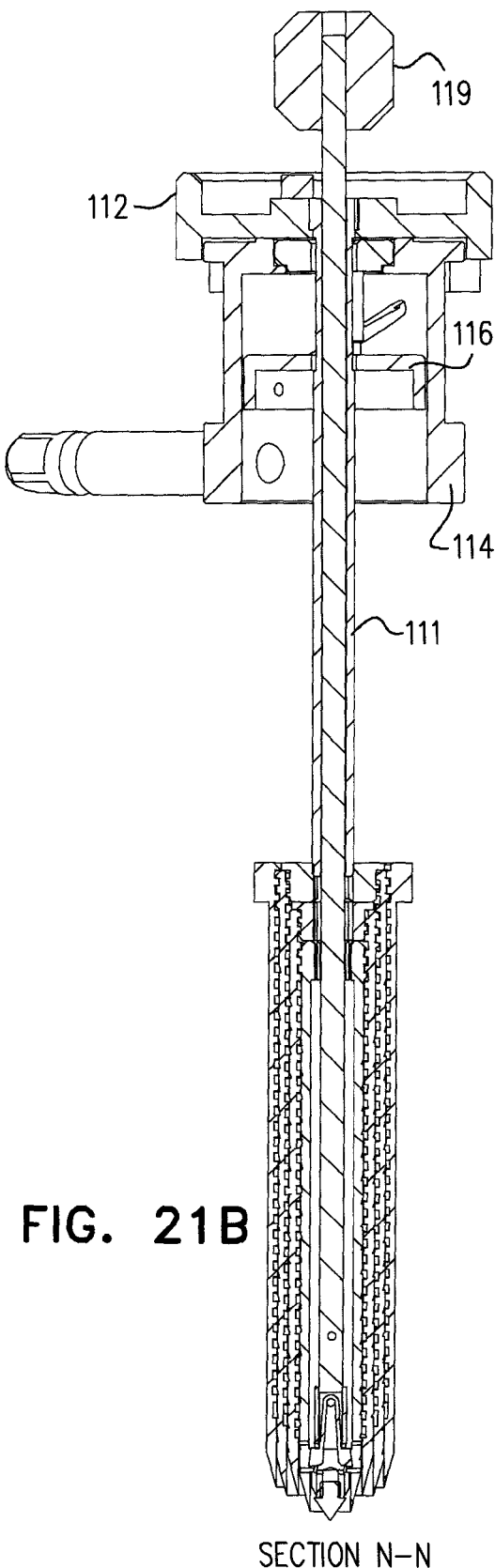

Referring first to FIG. 20, the positioning screws 117 are removed from the spiral groove in the cylindrical enclosure 114. Then in FIG. 21, there is shown that the cylindrical enclosure 114, together with the top cover 116 of the outermost spreader 91 can be raised, leaving only the nest of spreaders and the splined drive shaft 111, held in the patient's tissues.

Figure 22A:
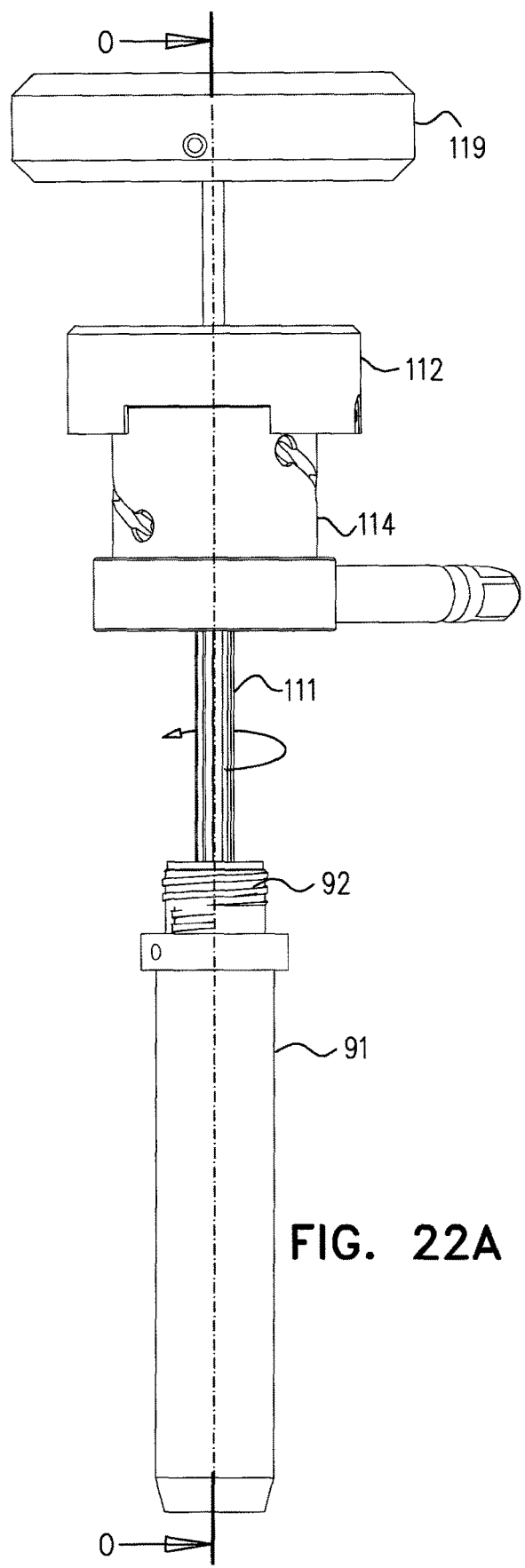
Figure 22B:
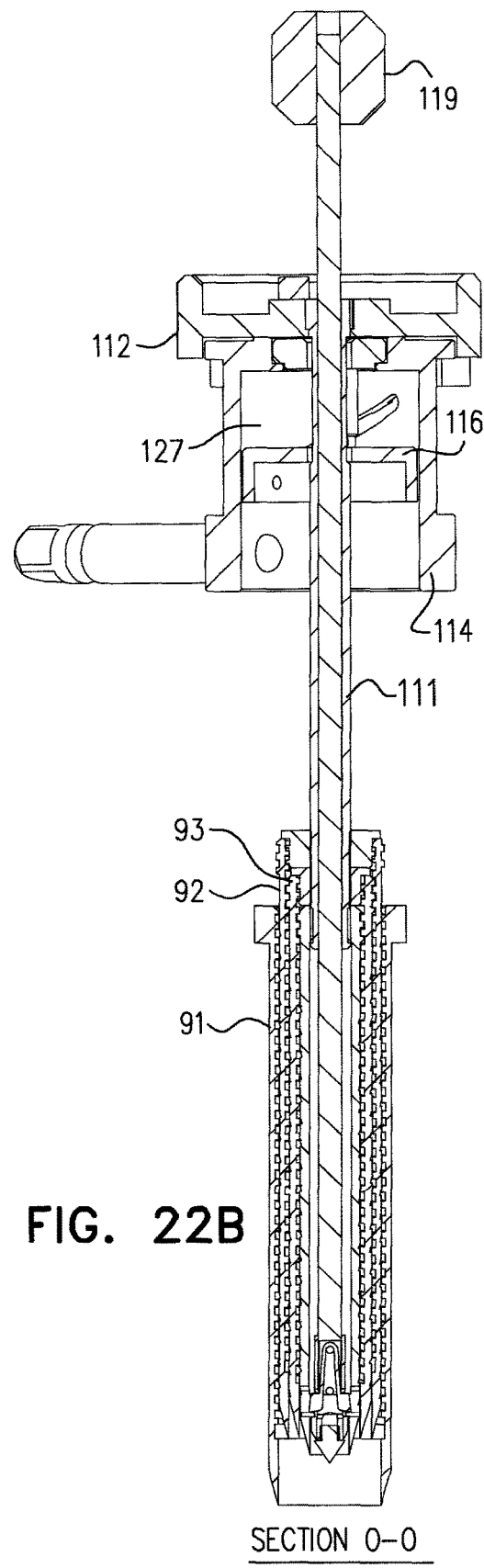

Reference is now made to FIG. 22, which shows how, by rotation of the splined drive shaft 111, together with the spiked rod, in an anticlockwise direction, all of the spreaders 92, 93, 94, and other components internal to or attached to the outermost spreader 91, screw out of the outermost spreader 91, leaving it alone penetrated through the patient's skin 113, and fixed in the patient's tissue, as shown in FIG. 23.

As previously mentioned, in this described implementation, all of the motion steps are described only as mechanical motion steps without reference to the manner in which these steps are performed. It is to be understood that the disclosure is intended only to explain the mechanical steps necessary in order to deploy the described auto dilator. In this respect, although manual operation may be the simplest way of using the device, it is to be understood that the disclosure is in no way intended to limit the device to such use. Thus, if the device is to be completely automated, such that it could be used on a robotic surgical system, rotary and linear actuators could be used for each rotary or linear motion step, with the sequence being controlled and monitored by means of a robotic controller, and sensors or encoders incorporated on the various mechanical parts. For instance, the use of manually adjusted positioning screws 117 in a spiral groove 101 in the cylindrical enclosure 114 could readily be replaced by any other method of controlling and locking the longitudinal motion required. Thus, for instance, a motorized linear motion drive could readily be used in fully robotic operation of the auto-dilator. The various rotary motions could also readily be replaced by at least some of servomotors with rotary encoders and position sensors.

This second exemplary implementation of the automatic dilators described in this disclosure has a possible disadvantage or inconvenience in that the longitudinal position of the cylindrical enclosure 114 has to be shifted by means of the positioning screws 117, or an alternative positioning mechanism, to enable deployment of successive spreaders.

Figure 24:
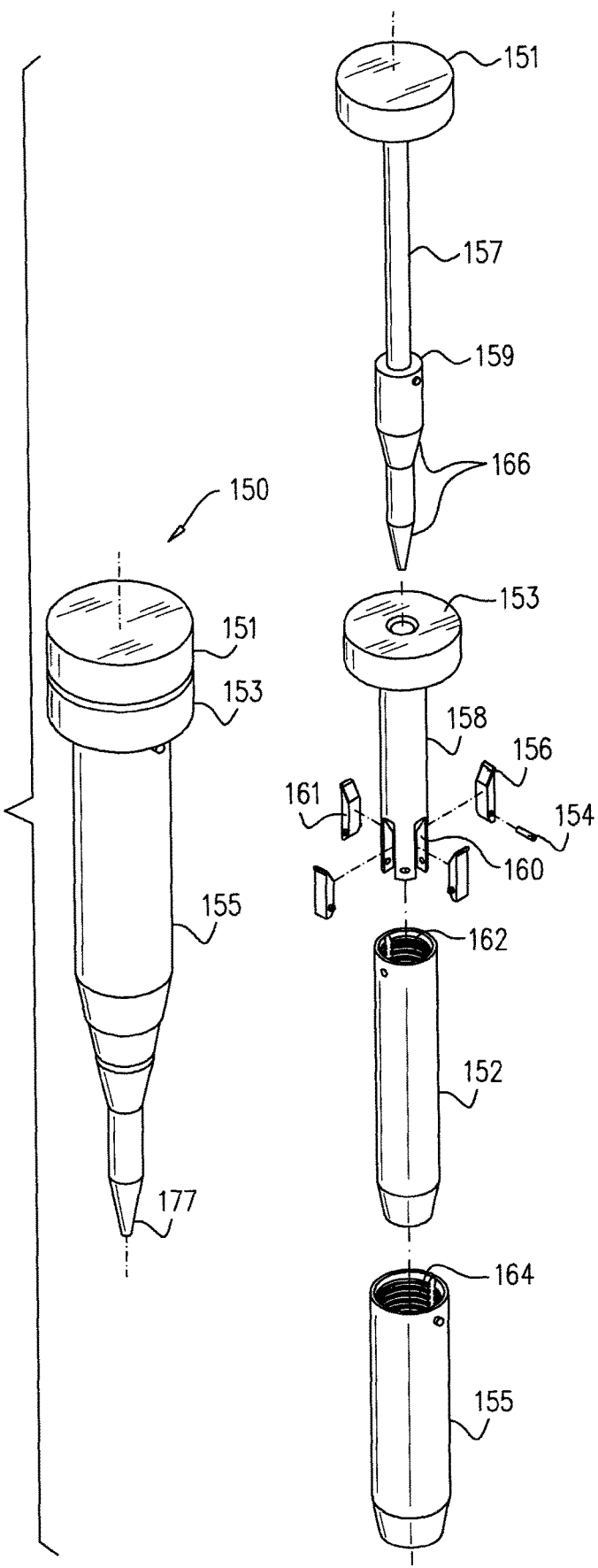
FIG. 24 is a schematic assembly drawing of a third exemplary implementation of the automatic dilators described in this disclosure, using a series of spring loaded external pawls to switch the linear motion from one spreader to the next.

Reference is now made to FIG. 24 which illustrates schematically a third exemplary implementation of an automatic dilator as described in this disclosure, in which the complete insertion procedure is performed by one continuous screwing motion. FIGS. 25 to 27 illustrate how the dilator of FIG. 24 operates through its various stages of insertion into the subject's tissue. The exemplary dilator shown in FIGS. 24 to 27 has an internal dilation rod with only two spreaders external thereto, but it is to be understood that this is only one example, and that the device could have a larger number of spreaders to increase its expansion range.

Like the previously described examples, this implantation also depends upon the rotation of the thread form of an inner element meshed with the thread form of the spreader tube element immediately external to it, such that as the inner thread form is rotated, if the outer spreader tube is prevented from rotating, it will move longitudinally and into the subject's tissue. This implementation differs from the previous ones in that the rotating inner thread takes the form of a set of radially positioned, spring-loaded, hinged pawl elements, each having a toothed protrusion which meshes with the inner thread of the spreader immediately external to it, driving it distally into the tissue as the toothed protrusions rotate. As soon as the immediately external spreader element reaches its distal deployed location, the toothed protrusions on the hinged pawl elements slip off the end of the internal thread on that first spreader element, and being spring-loaded in an outward direction, now mesh with the internal thread on the next outwardly positioned spreader element, and rotation of the innermost element now begins to move that next outwardly positioned spreader longitudinally into the tissue.

In FIG. 24, there is shown an assembled and an exploded isometric view of an exemplary design of this implementation of the complete auto dilator 150, showing its component parts. The innermost element of the device is the spiked rod 157, which has a sharpened spike 177 at its distal end. This is the embodiment shown in the assembled drawing on the right hand side of FIG. 24. According to an alternative implementation, in order to ease insertion of the spiked rod into the patient's tissue, a number of graded chamfers 166 can be provided to the spiked rod 157, as shown in the exploded unassembled view on the left hand side of FIG. 24, to expand its diameter to the internal diameter of the first spreader tube 152. In this case, the first spreader tube 152 should be allowed to extend only along the parallel section of the spiked rod, to avoid unnecessary trauma to the patient's tissue as it is inserted. A handle 151 is provided at the proximal end of the spiked rod. The spiked rod is incorporated within an actuating tube 158, which has an internal bore adapted to take the spiked rod. In the example shown in FIG. 24, the actuating tube 158 sits on a shoulder 159 on the spiked rod, so that the enlarged outer diameter of the spiked rod is contiguous with the outer diameter of the actuating tube 158. In the construction shown in FIG. 24, the spiked rod 157, with its distal spiked spreader point needs to be dismountable in order for it to be inserted into the actuating tube 158. The actuating tube 158 has its own rotation handle 153 at its proximal end.

At its distal end, the actuating tube has a number of grooved longitudinal indentations 160, four in number in the example shown in FIG. 24, though it is to be understood that any other practical number of such grooved indentations could be provided, even a single indentation. In each of these grooved indentations 160, there is fitted a spring loaded pawl element 156, hinged on a pin 54 such that the pawl element 156 is enabled to swing in an outwards direction. The pawl elements 156 are fitted with an internal spring (not shown) which biases them in the outward direction. The pawl elements 156 each have an externally protruding tooth 161 at the end opposite to that at which they are hinged.

The entire inner assembly comprising the spiked rod 157 and the actuating tube 158 with its spring-loaded pawl elements 156, is located within the inner bore of the first spreader element 152, with its chamfered distal end. This spreader element has an internal thread 162 and the externally protruding teeth 161 of the spring-loaded pawl elements 156 fit into the internal thread 162. The externally protruding teeth 161 should be in axially staggered positions such that they are positioned to all fit correctly into the internal thread 162, even though they contact the internal thread at different circumferential orientations.

External and concentrically to the first spreader element 152, there is located a second spreader element 155, also having an internal thread form 164, and although no further spreader elements are shown in the device of FIG. 24, it is to be understood that more spreaders could be incorporated external to second spreader element 155.

Reference is now made to FIGS. 25 to 27, which include assembled and cut away sections of the assembled auto dilator of FIG. 24, to illustrate how the device operates in use. In FIG. 25, section A-A shows the assembled auto dilator 150, with the operative structure of one of the spring-loaded pawl elements 156 shown in blown-up detail. Referring to this blown-up drawing, the spring-loaded pawl element 156 is shown with its protruding tooth 161 lodged in the internal thread 162 of the first spreader element 152. In order to deploy the auto dilator, after the spiked rod 157 has been inserted into the tissue to the depth required, the rotation handle 153 of the first spreader element 152 is turned while the handle 151 of the spiked rod 157 is held stationary, in case the friction of the spiked rod 157 and its spike 177 stuck into the subject's tissue does not hold it stationary. As the first spreader element 152 rotates, the static protruding tooth 161 riding in its internal thread, causes the first spreader element 152 to move distally over the spiked rod and into the tissue, widening the opening in the tissue. Section B-B shows the device in axially directed cross section.

Reference is now made to FIG. 26, which shows the first spreader element 152 almost fully deployed, with the protruding teeth 161 of the spring-loaded pawl elements 156 still riding in the internal thread 162 of the first spreader element 152. The blown-up detailed drawing shows this clearly.

Reference is now made to FIG. 27, which shows the situation when the first spreader element 152 has reached its most distal deployed position. The length of the spreader element 152 and hence of the internal thread 162 of the first spreader element, is adapted to be such that as the spreader element reaches its fully deployed position, the toothed protrusion 161 of the spring-loaded pawl 156 jumps out of the internal thread 162 in an outwards direction because of its spring loading, until it lodges within a groove at the distal end of the internal thread 164 of the second spreader element 155, as shown in the blown-up detailed drawing. As the handle 153 continues to rotate, together with the toothed protrusion, the second spreader tube 155 now starts to move distally over the previously deployed first spreader element 152, actuated by the protruding tooth 161 now riding in the internal thread 164 of the second spreader tube 155.

Once the second spreader tube is fully deployed, further spreader tubes can be sequentially installed, with the toothed protrusions of the spring-loaded pawls jumping from one internal thread to the next in outward going order as each spreader tube completes its insertion and releases the protruding tooth element 161 from its own thread to spring further out to engage the internal thread in the next outwardly positioned spreader tube.

Although this third implementation has been described using a toothed projection on a hinged, spring loaded pawl as the element used for engaging the inner threads of the consecutive spreader tubes, it is to be understood that this is only one exemplary method by which to achieve engagement with the internal thread form. The invention is not intended to be limited thereto, but includes any alternative structure involving an externally protruding tooth, or teeth, which are rotated so as to cause the internal threaded element with which it or they engage to move distally.

This implementation thus enables insertion of a sequence of spreader tubes by means of a continuous rotation action, without the need for any intermediate action in order to switch from one spreader tube to the next. This implementation is therefore suitable for a simple robotically actuated entry procedure.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. An automatic dilator device, comprising:
a plurality of concentric spreader tubes and an inner rotatable element, the automatic dilator device configured to use rotary coupling of each of the spreader tubes to either (a) another adjacent spreader tube or (b) the inner rotatable element, to drive each of the concentric spreader tubes longitudinally, each of the spreader tubes and the rotatable element comprising a coupling mechanism configured to enable the coupling;
the coupling mechanism comprising one of:
(i) a thread engaging element on an external surface of one of the spreader tubes, and a helical thread formed on at least a majority of a length of an inner surface of an adjacent one of the spreader tubes;
(ii) a thread engaging element on an inner surface of one of the spreader tubes, and a helical thread formed on at least a majority of a length of an external surface of an adjacent one of the spreader tubes; and
(iii) a deployable thread engaging element on the inner rotatable element, and a helical thread formed on at least a majority of a length of an inner surface of one of the spreader tubes external to the inner rotatable element;
wherein the automatic dilator device further comprises a mechanical transfer mechanism configured to provide automatic sequential deployment of the plurality of concentric spreader tubes, by transferring the rotary coupling to a second one of the spreader tubes once a first one of the spreader tubes has reached a required position.

2. The automatic dilator device of claim 1, wherein the coupling mechanism comprises option (i) or (ii), the device further comprising a splined drive shaft disposed axially through the spreader tubes and adapted to mesh sequentially with an internally splined section associated with each of the spreader tubes, such that rotation of the splined drive shaft causes one of the spreader tubes with which the splined draft shaft is meshed to rotate.

3. The automatic dilator device of claim 2, wherein the splined drive shaft has a proximal end comprising an unsplined section, and the plurality of concentric spreader tubes are of such lengths that the unsplined section does not mesh with the internally splined section associated with any spreader tube that is not yet required to rotate.

4. The automatic dilator device of claim 2, wherein the transfer mechanism comprises an axial motion mechanism that moves axially to selectively prevent or allow rotary motion of any of the spreader tubes.

5. The automatic dilator device of claim 4, wherein the splined draft shaft comprises a splined section and an unsplined section, and further wherein the axial motion mechanism is configured to move the splined drive shaft in a proximal direction such that the splined section meshes with the internally splined section associated with a spreader tube that is required to be rotated, the internally splined section being previously disposed opposite the unsplined section of the splined drive shaft.

6. The automatic dilator device of claim 4, wherein the axial motion mechanism comprises at least one axially moveable pin disposed off-axis to an innermost spreader tube of the plurality of concentric spreader tubes, such that the axial motion is adapted to insert the at least one axially moveable pin into at least one off-axis aperture at a distal end of the innermost spreader tube to selectively prevent rotation of the innermost spreader tube.

7. The automatic dilator device of claim 2, wherein the splined drive shaft has a length such that when a spreader tube reaches a predetermined deployed position, the internal splined section associated with the spreader tube slips off an end of the splined drive shaft and out of engagement with the splined drive shaft, such that the spreader tube is no longer rotated by the splined drive shaft.

8. The dilator device of claim 2, wherein the splined drive shaft is adapted to be rotated by a robotic rotation mechanism.

9. The automatic dilator device of claim 1, wherein the coupling mechanism comprises option (iii), the device further comprising:
   a spiked rod disposed within the inner rotatable element, wherein the deployable thread engaging element is at least one outwardly biased tooth element;
   wherein rotation of the inner rotatable element is adapted to cause the at least one outwardly biased tooth element to move the innermost spreader tube longitudinally in a distal direction, until the at least one outwardly biased tooth element springs outwardly off the proximal end of the helical thread formed on the inside surface of the innermost spreader tube, and onto the helical thread formed on the inside surface of the next outwardly positioned spreader tube.

10. The automatic dilator device of claim 9 wherein at least one of the outwardly biased tooth elements is a hinged pawl element incorporated into the inner rotatable element, spring loaded such that it has an outwardly directed force acting on its end remote from a hinge, and having an externally protruding tooth which meshes with the helical thread formed on the inside surface of the spreader tube immediately external to it.

11. The automatic dilator device of claim 9, wherein the spiked rod is adapted to be rotated by a robotic rotation mechanism.

12. The automatic dilator device of claim 1, wherein the automatic dilator device is adapted to be operated by continuous rotary motion in one direction, as supplied by a surgical drill or a robotic rotary drive, such that the plurality of concentric spreader tubes are inserted into a patient.

13. The automatic dilator device of claim 1, wherein the automatic dilator device is adapted to be used with a robotic surgical system, the system comprising rotary and linear actuators for rotary and linear motion steps of the device.

14. The automatic dilator device of claim 1, wherein the thread engaging element is any one of a protrusion element, an outwardly biased tooth element, a section of thread form, a set of one or more teeth or a set of one or more tabs.

15. An automatic dilator device, comprising:
   a plurality of concentric spreader tubes;
   an inner rotatable element;
   means for coupling each of the plurality of concentric spreader tubes to either (a) an adjacent spreader tube or (b) the inner rotatable element in order to drive each of the plurality of concentric spreader tubes longitudinally, the means for coupling comprising:
   a thread engaging element on either (a) an external surface of one of the plurality of concentric spreader tubes or (b) an external surface of the inner rotatable element; and
   a helical thread formed on at least a majority of a length of an inner surface of an external one of the plurality of concentric spreader tubes;
   wherein the means for coupling enables automatic sequential deployment of the plurality of concentric spreader tubes by rotatably coupling a second one of the plurality of concentric spreader tubes once a first one of the plurality of concentric spreader tubes has reached a predetermined driven position.

16. The automatic dilator device of claim 15, wherein the thread engaging element is a deployable thread engaging element on the inner rotatable element.

17. An automatic dilator device, comprising:
   a plurality of concentric spreader tubes;
   an inner rotatable element;
   means for coupling each of the plurality of concentric spreader tubes to either (a) an adjacent spreader tube or (b) the inner rotatable element in order to drive each of the plurality of concentric spreader tubes longitudinally, the means for coupling comprising:
   a thread engaging element on an inner surface of one of the plurality of concentric spreader tubes; and
   a helical thread formed on at least a majority of a length of an external surface of an adjacent one of the plurality of concentric spreader tubes;
   wherein the means for coupling enables automatic sequential deployment of the plurality of concentric spreader tubes by rotatably coupling a second one of the plurality of concentric spreader tubes once a first one of the plurality of concentric spreader tubes has reached a predetermined driven position.

* * * * *